United States Patent [19]
Jepsen et al.

[11] Patent Number: 6,004,581
[45] Date of Patent: *Dec. 21, 1999

[54] MODIFIED RELEASE ORAL PHARMACEUTICAL COMPOSITION AND METHOD FOR THE TREATMENT OF BOWEL DISEASES

[75] Inventors: Svenn Klüver Jepsen, Holte; Søren Halskov, Virum, both of Denmark

[73] Assignee: Farmaceutisk Laboratorium Ferring A/S, Vanlose, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/772,273

[22] Filed: Dec. 20, 1996

Related U.S. Application Data

[60] Provisional application No. 60/045,788, Dec. 21, 1995, abandoned.

[51] Int. Cl.[6] .............................. A61K 9/58; A61K 9/62
[52] U.S. Cl. ...................... 424/461; 424/462; 424/495; 424/497
[58] Field of Search ................... 424/490, 462, 424/495, 497, 461

[56] References Cited

U.S. PATENT DOCUMENTS

| | | | |
|---|---|---|---|
| 4,496,553 | 1/1985 | Halskov | 514/166 |
| 4,960,765 | 10/1990 | Halskov | 514/166 |
| 4,980,173 | 12/1990 | Halskov | 424/490 |
| 5,294,448 | 3/1994 | Ring et al. | 424/497 |
| 5,401,512 | 3/1995 | Rhodes et al. | 424/458 |
| 5,716,648 | 2/1998 | Halskov et al. | 424/682 |

FOREIGN PATENT DOCUMENTS

| | | |
|---|---|---|
| WO91/07949 | 6/1991 | WIPO . |
| WO94/28911 | 12/1994 | WIPO . |

OTHER PUBLICATIONS

Bechgaard, H., Acta Pharmaceutica Technologica 28(2), 1982, pp. 149–157.
Fallingborg, J. et al, Aliment. Pharmacol. Therap. (1989) 3, pp. 605–613.
Christensen, L.A. et al, Br. J. Clin. Pharmac. (1987), 23, pp. 365–369.

Primary Examiner—Thurman K. Page
Assistant Examiner—L. Channavajjala
Attorney, Agent, or Firm—Jacobson, Price, Holman & Stern, PLLC

[57] ABSTRACT

Modified release pharmaceutical composition and method for the treatment of inflammatory bowel diseases (IBD) such as Crohn's disease and Colitis Ulccrosa, said compositions comprising as active the ingredient 5-aminosalicylic acid (5-ASA), and being adapted for modified and targeted release so as to obtain a clinically important localized effect profile of 5-ASA by means of releasing an appropriate amount of 5-ASA in both the small and large bowel.

37 Claims, 12 Drawing Sheets

Figure 1    Image Analysis of Spherical Granules (Batch 322202)

Analysis of geometrical characteristic of spherical granules (Batch322202)

| No | Length | Breadth | Peri-meter | Aspect Ration | No | Length | Breadth | Peri-meter | Aspect Ration | No | Length | Breadth | Peri-meter | Aspect Ration |
|---|---|---|---|---|---|---|---|---|---|---|---|---|---|---|
| 1 | 0.829 | 0.777 | 2.617 | 1.066 | 1 | 0.894 | 0.829 | 2.811 | 1.078 | 1 | 0.777 | 0.738 | 2.487 | 1.052 |
| 2 | 0.842 | 0.712 | 2.513 | 1.181 | 2 | 0.933 | 0.855 | 2.927 | 1.090 | 2 | 0.946 | 0.868 | 2.979 | 1.089 |
| 3 | 0.842 | .0777 | 2.655 | 1.083 | 3 | 0.933 | 0.855 | 2.902 | 1.090 | 3 | 0.894 | 0.803 | 2.746 | 1.112 |
| 4 | 0.803 | 0.699 | 2.500 | 1.148 | 4 | 0.855 | 0.803 | 2.694 | 1.064 | 4 | 0.933 | 0.842 | 2.850 | 1.107 |
| 5 | 0.881 | 0.777 | 2.746 | 1.133 | 5 | 0.881 | 0.803 | 2.746 | 1.096 | 5 | 0.829 | 0.764 | 2.591 | 1.084 |
| 6 | 0.842 | 0.751 | 2.578 | 1.120 | 6 | 0.712 | 0.661 | 2.267 | 1.078 | 6 | 0.946 | 0.855 | 2.940 | 1.106 |
| 7 | 0.816 | 0.777 | 2.604 | 1.050 | 7 | 0.894 | 0.842 | 2.824 | 1.061 | 7 | 0.894 | 0.803 | 2.733 | 1.112 |
| 8 | 0.933 | 0.855 | 2.927 | 1.090 | 8 | 0.751 | 0.661 | 2.319 | 1.137 | 8 | 0.868 | 0.790 | 2.746 | 1.098 |
| 9 | 0.777 | 0.687 | 2.396 | 1.132 | 9 | 0.829 | 0.764 | 2.617 | 1.084 | 9 | 0.907 | 0.855 | 2.837 | 1.060 |
| 10 | 0.946 | 0.868 | 2.979 | 1.089 | 10 | 0.803 | 0.764 | 2.539 | 1.050 | 10 | 0.920 | 0.855 | 2.876 | 1.075 |
| 11 | 1.101 | 0.881 | 3.251 | 1.250 | 11 | 0.946 | 0.855 | 2.953 | 1.106 | 11 | 0.933 | 0.803 | 2.863 | 1.161 |
| 12 | 0.829 | 0.777 | 2.617 | 1.066 | 12 | 1.023 | 0.868 | 3.135 | 1.179 | 12 | 0.920 | 0.829 | 2.863 | 1.109 |
| 13 | 0.946 | 0.816 | 2.927 | 1.158 | 13 | 0.855 | 0.777 | 2.668 | 1.100 | 13 | 0.816 | 0.725 | 2.487 | 1.125 |
| 14 | 0.984 | 0.829 | 2.772 | 1.078 | 14 | 0.816 | 0.751 | 2.513 | 1.086 | 14 | 0.894 | 0.790 | 2.746 | 1.131 |
| 15 | 0.842 | 0.764 | 2.668 | 1.101 | 15 | 0.842 | 0.816 | 2.720 | 1.031 | 15 | 0.829 | 0.751 | 2.617 | 1.103 |
| 16 | 0.907 | 0.738 | 2.694 | 1.228 | 16 | 0.881 | 0.803 | 2.772 | 1.096 | 16 | 0.933 | 0.894 | 2.979 | 1.043 |
| 17 | 0.907 | 0.803 | 2.772 | 1.129 | 17 | 0.946 | 0.868 | 2.915 | 1.089 | 17 | 0.907 | 0.868 | 2.927 | 1.044 |
| 18 | 0.972 | 0.920 | 3.070 | 1.056 | 18 | 0.803 | 0.751 | 2.578 | 1.068 | 18 | 0.751 | 0.674 | 2.319 | 1.115 |
| 19 | 0.881 | 0.816 | 2.811 | 1.079 | 19 | 0.920 | 0.842 | 2.876 | 1.092 | 19 | 0.855 | 0.777 | 2.642 | 1.100 |
| 20 | 0.972 | 0.816 | 2.953 | 1.190 | 20 | 0.842 | 0.751 | 2.578 | 1.120 | 20 | 0.816 | 0.777 | 2.604 | 1.050 |
| 21 | 0.907 | 0.842 | 2.876 | 1.076 | 21 | 0.868 | 0.829 | 2.759 | 1.046 | 21 | 0.907 | 0.868 | 2.889 | 1.044 |
| 22 | 0.790 | 0.712 | 2.448 | 1.109 | 22 | 0.907 | 0.881 | 2.915 | 1.029 | 22 | 0.816 | 0.738 | 2.513 | 1.105 |
| 23 | 1.075 | 0.881 | 3.174 | 1.220 | 23 | 0.881 | 0.816 | 2.811 | 1.079 | 23 | 0.842 | 0.751 | 2.578 | 1.120 |
| 24 | 0.920 | 0.790 | 2.824 | 1.163 | 24 | 0.855 | 0.790 | 2.746 | 1.081 | 24 | 0.920 | 0.829 | 2.824 | 1.109 |
| 25 | 0.959 | 0.855 | 2.927 | 1.121 | 25 | 0.907 | 0.829 | 2.837 | 1.093 | 25 | 0.855 | 0.738 | 2.642 | 1.157 |
| Mean | 0.897 | 0.797 | 2.772 | 1.125 | Mean | 0.871 | 0.803 | 2.737 | 1.085 | Mean | 0.876 | 0.799 | 2.731 | 1.096 |
| St. Dev. | 0.081 | 0.061 | 0.221 | 0.056 | St. Dev. | 0.066 | 0.058 | 0.198 | 0.032 | St. Dev. | 0.055 | 0.056 | 0.176 | 0.033 |
| Max. | 1.101 | 0.920 | 3.251 | 1.250 | Max. | 1.023 | 0.881 | 3.135 | 1.179 | Max. | 0.946 | 0.894 | 2.979 | 1.161 |
| Min. | 0.777 | 0.687 | 2.396 | 1.050 | Min. | 0.712 | 0.661 | 2.267 | 1.029 | Min. | 0.751 | 0.674 | 2.319 | 1.043 |
| | | | | | | | | | | Mean | 0.881 | 0.800 | 2.747 | 1.102 |
| | | | | | | | | | | St. Dev. | 0.068 | 0.058 | 0.197 | 0.044 |
| | | | | | | | | | | Max. | 1.101 | 0.920 | 3.251 | 1.250 |
| | | | | | | | | | | Min. | 0.751 | 0.674 | 2.319 | 1.029 |

Batch
Batch no.: 322202

FIG. 2

Figure 3    Image Analysis of Spherical Granules (Batch 437601)

Analysis of geometrical characteristics of spherical granules (Batch 437601)

| No | Length | Breadth | Perimeter | Aspect Ration | No | Length | Breadth | Perimeter | Aspect Ration | No | Length | Breadth | Perimeter | Aspect Ration |
|---|---|---|---|---|---|---|---|---|---|---|---|---|---|---|
| 1 | 0.725 | 0.674 | 2.319 | 1.076 | 1 | 0.687 | 0.609 | 2.111 | 1.127 | 1 | 0.842 | 0.777 | 2.642 | 1.083 |
| 2 | 0.803 | 0.751 | 2.526 | 1.068 | 2 | 0.842 | 0.777 | 2.655 | 1.083 | 2 | 0.868 | 0.790 | 2.668 | 1.098 |
| 3 | 0.712 | 0.661 | 2.241 | 1.078 | 3 | 0.946 | 0.829 | 2.902 | 1.140 | 3 | 0.881 | 0.816 | 2.772 | 1.079 |
| 4 | 0.946 | 0.842 | 2.953 | 1.123 | 4 | 0.933 | 0.868 | 2.927 | 1.074 | 4 | 0.777 | 0.687 | 2.370 | 1.132 |
| 5 | 0.959 | 0.868 | 2.966 | 1.104 | 5 | 0.803 | 0.725 | 2.513 | 1.107 | 5 | 0.764 | 0.648 | 2.306 | 1.180 |
| 6 | 0.920 | 0.868 | 2.876 | 1.059 | 6 | 0.816 | 0.764 | 2.565 | 1.067 | 6 | 0.907 | 0.751 | 2.720 | 1.206 |
| 7 | 0.868 | 0.790 | 2.720 | 1.098 | 7 | 0.777 | 0.674 | 2.345 | 1.153 | 7 | 0.997 | 0.907 | 3.109 | 1.100 |
| 8 | 0.933 | 0.881 | 2.992 | 1.058 | 8 | 0.894 | 0.842 | 2.811 | 1.061 | 8 | 0.842 | 0.777 | 2.591 | 1.083 |
| 9 | 0.842 | 0.803 | 2.694 | 1.048 | 9 | 0.738 | 0.583 | 2.189 | 1.266 | 9 | 0.790 | 0.738 | 2.513 | 1.070 |
| 10 | 0.907 | 0.803 | 2.850 | 1.129 | 10 | 0.816 | 0.712 | 2.422 | 1.145 | 10 | 0.868 | 0.803 | 2.733 | 1.080 |
| 11 | 0.842 | 0.764 | 2.642 | 1.101 | 11 | 0.790 | 0.751 | 2.526 | 1.051 | 11 | 0.933 | 0.855 | 2.902 | 1.090 |
| 12 | 0.829 | 0.738 | 2.552 | 1.122 | 12 | 0.790 | 0.777 | 2.565 | 1.016 | 12 | 0.816 | 0.712 | 2.487 | 1.145 |
| 13 | 0.933 | 0.829 | 2.915 | 1.125 | 13 | 0.829 | 0.687 | 2.500 | 1.207 | 13 | 0.855 | 0.803 | 2.707 | 1.064 |
| 14 | 0.790 | 0.764 | 2.526 | 1.033 | 14 | 0.751 | 0.699 | 2.370 | 1.074 | 14 | 0.842 | 0.777 | 2.617 | 1.083 |
| 15 | 0.790 | 0.751 | 2.539 | 1.051 | 15 | 0.803 | 0.687 | 2.396 | 1.169 | 15 | 0.816 | 0.777 | 2.591 | 1.050 |
| 16 | 0.868 | 0.764 | 2.681 | 1.135 | 16 | 0.816 | 0.764 | 2.591 | 1.067 | 16 | 0.907 | 0.855 | 2.863 | 1.060 |
| 17 | 0.816 | 0.738 | 2.539 | 1.105 | 17 | 0.738 | 0.661 | 2.306 | 1.117 | 17 | 0.712 | 0.648 | 2.215 | 1.100 |
| 18 | 0.803 | 0.738 | 2.487 | 1.087 | 18 | 0.790 | 0.751 | 2.539 | 1.051 | 18 | 1.010 | 0.868 | 3.057 | 1.164 |
| 19 | 0.842 | 0.764 | 2.604 | 1.101 | 19 | 0.803 | 0.712 | 2.422 | 1.127 | 19 | 0.881 | 0.842 | 2.850 | 1.046 |
| 20 | 0.751 | 0.687 | 2.370 | 1.094 | 20 | 0.868 | 0.790 | 2.707 | 1.098 | 20 | 0.790 | 0.712 | 2.461 | 1.109 |
| 21 | 0.816 | 0.738 | 2.513 | 1.105 | 21 | 0.751 | 0.674 | 2.306 | 1.115 | 21 | 0.881 | 0.816 | 2.720 | 1.079 |
| 22 | 0.842 | 0.764 | 2.655 | 1.101 | 22 | 0.712 | 0.648 | 2.241 | 1.100 | 22 | 0.790 | 0.738 | 2.461 | 1.070 |
| 23 | 0.829 | 0.751 | 2.565 | 1.103 | 23 | 0.984 | 0.855 | 3.005 | 1.151 | 23 | 0.803 | 0.764 | 2.552 | 1.050 |
| 24 | 0.790 | 0.712 | 2.435 | 1.109 | 24 | 0.842 | 0.764 | 2.668 | 1.101 | 24 | 0.816 | 0.790 | 2.630 | 1.032 |
| 25 | 0.777 | 0.622 | 2.306 | 1.250 | 25 | 0.816 | 0.764 | 2.565 | 1.067 | 25 | 0.894 | 0.829 | 2.772 | 1.078 |
| Mean | 0.837 | 0.763 | 2.619 | 1.099 | Mean | 0.813 | 0.735 | 2.526 | 1.109 | Mean | 0.851 | 0.779 | 2.652 | 1.093 |
| St. Dev. | 0.067 | 0.065 | 0.213 | 0.042 | St. Dev. | 0.071 | 0.073 | 0.228 | 0.054 | St. Dev. | 0.069 | 0.065 | 0.214 | 0.043 |
| Max. | 0.959 | 0.881 | 2.992 | 1.250 | Max. | 0.984 | 0.868 | 3.005 | 1.266 | Max. | 1.010 | 0.907 | 3.109 | 1.206 |
| Min. | 0.712 | 0.622 | 2.241 | 1.033 | Min. | 0.687 | 0.583 | 2.111 | 1.016 | Min. | 0.712 | 0.648 | 2.215 | 1.032 |
|  |  |  |  |  |  |  |  |  |  | Mean | 0.834 | 0.759 | 2.599 | 1.100 |
|  |  |  |  |  |  |  |  |  |  | St. Dev. | 0.070 | 0.069 | 0.222 | 0.046 |
|  |  |  |  |  |  |  |  |  |  | Max. | 1.010 | 0.907 | 3.109 | 1.266 |
|  |  |  |  |  |  |  |  |  |  | Min. | 0.712 | 0.648 | 2.215 | 1.016 |

Batch no.: 437601

FIG. 4

Disposition data of Spherical Granules (Batch 437601)

|  | Gastric Emptying Time (mins) | | Colon Arrival Time (mins) | |
| --- | --- | --- | --- | --- |
|  | $T_{50\%}$ | $T_{100\%}$ | $T_{50\%}$ | $T_{100\%}$ |
| 1 | 22 | 60 | 100 | 121 |
| 2 | 33 | 124 | 308 | 727 |
| 3 | 10 | 83 | 260 | 513 |
| 4 | 25 | 65 | 200 | 277 |
| 5 | 38 | 124 | 253 | 261 |
| 7 | 17 | 73 | 292 | 469 |
| 8 | 13 | 65 | 154 | 172 |
| 9 | 15 | 30 | 82 | 180 |
| Mean | 22 | 78 | 206 | 340 |
| SD | 10 | 32 | 86 | 210 |
| RSD % | 46 | 41 | 42 | 62 |
| Median | 20 | 69 | 227 | 269 |

FIG. 10

MODIFIED RELEASE ORAL PHARMACEUTICAL COMPOSITION AND METHOD FOR THE TREATMENT OF BOWEL DISEASES

CROSS-REFERENCE TO RELATED APPLICATIONS

This application is based on provisional application Ser. No. 60/045,788, filed Dec. 21, 1995, now abandoned.

FIELD OF THE INVENTION

The present invention provides improved oral pharmaceutical compositions for the treatment of inflammatory bowel diseases (IBD) such as Crohn's disease, Colitis Ulcerosa and related diseases, e.g. an unclassifiable form of said diseases or a diagnosed subtype of one of said diseases. The invention also provides a method for the treatment of IBD.

The composition of the present invention comprises as active ingredient 5-aminosalicylic acid (5-ASA) or pharmaceutically acceptable salts or esters thereof and is adapted for modified and targeted release of said 5-ASA in the diseased parts of the intestine, so as to obtain an advantageous and clinically important release and effect profile of 5-ASA. Thus, said administration form and release are improved compared to known therapy regimens.

BACKGROUND OF THE INVENTION

The composition of the invention is individually coated granules adapted for oral administration as such, i.e. the composition is a "granulate" composition ready for use. The granule composition of the invention is an advantageous administration form in many clinical situations, e.g. with respect to patient having difficulties in swallowing and with respect to children not wanting to swallow tablets.

A further advantage is that the granules or the invention may be packaged in unit dosage forms comprising larger amounts of active 5-ASA, e.g. in sachets or sticks.

In principle, there is, in contrast to the maximal content of tablets and capsules, no upper limit to the amount of active ingredients in a unit dosage form of the composition according to the invention.

Thus, an advantage of the granule composition of the present invention is that it enables improved compliance values with respect to the therapy regimen, a clinically important parameter for the treatment of chronic diseases.

Overall, it should be noted that the question of a satisfactory compliance is especially important in the case of IBD, since failure to respond to medical treatment in many cases necessitates surgery, with the standard surgical operation in the treatment of ulcerative colitis in many cases being total proctocolectomy (removal of the colon and the rectum).

U.S. Pat. Nos. 4,496,553 and 4,980,173 (Halskov) provide a method for the treatment of IBD by oral administration of 5-ASA compositions consisting essentially of free 5-ASA and carriers which will control the release of an effective amount of 5-ASA.

However, as opposed to the present invention, no mention of the administration of 5-ASA granules as such was disclosed, and the compositions described for clinical use were all in the form of tablets. The disclosure of said U.S. patents, including the examples, is totally silent about the provision of a specific type of granule composition for direct oral intake. Nowhere in said patent specification is it suggested to develop or administer a granule composition.

Thus, in the examples of the above U.S. patents, preparations of granulates pressed to form tablets with a diameter of 13.5 mm and a weight of 650 mg/tablet containing 250 mg of 5-AsA. The resulting tablets were used in clinical tests.

In the examples of the U.S. patents, two intermediary preparations of granulates were described, one of them comprising 5-ASA, and the other being a "helper" granulate without 5-ASA, said "helper" granulate being prepared and admixed in order to facilitate the tablet compression involving the addition of talc and a lubricant mixture.

The 173 patent more specifically claims a method for the preparation of sustained-release tablets, useful for the treatment of colitis ulcerosa or Crohn's disease, comprising the steps of a) preparing a first granulate from 5-ASA or a pharmaceutically acceptable salt or ester thereof and bout 10% by weight (solids content based on the 5-ASA) of polyvinylpyrrolidone in an organic solvent thereby to provide granules of a particle size from about 0.7 to 1 mm, upon evaporation of the solvent.

b) applying onto said granules a coating composition, comprising a solution in an organic solvent of a pharmaceutically acceptable coating material which will gradually release the active ingredient upon arrival at the small intestine, thereby to provide coated granules upon evaporation of the solvent, c) mixing the first granulate with about 5% by weight, calculated on the total solids content, of a lubricant and a conventional pharmaceutical tablet carrier in an amount in accordance with the desired size and active ingredient content of the tablet, and d) forming tablets from the resulting mixture Preferably the coating material is a cellulose derivative.

The specific requirements to the 5-ASA release properties of the granule composition as identified by the present inventors and defined by the present invention, were nowhere described or suggested in said U.S. patents, let alone any hint or guidance as to how to arrive at the specific embodiments of the invention, said embodiments solving the problems identified and thus providing advantages in a non-predictable way.

SUMMARY OF THE INVENTION

Surprisingly, according to the present invention, particular geometrical shapes of each of the granules in combination with the choice of and mixing of particular types of helper ingredients, provide granules with an especially advantageous and clinically important 5-ASA gastrointestinal release.

Surprisingly, the granule composition of the present invention provides an advantageous release profile securing a clinically important bio-availability. Such a useful bio-availability is obtained due to the following characteristics: only a minor release of 5-ASA in the stomach is obtained, whereas a considerable amount of 5-ASA is available for an appropriate period of time in the small intestine, and also a considerably amount of 5-ASA is available in the large intestine.

Thus, in one of its main aspects, the invention provides a composition for oral administration, said composition being:

an oral modified release composition ensuring bioavailability of said 5-ASA in both the small and large intestine, and comprising:

individually coated granules, each granule comprising:

a core comprising 5-aminosalicylic acid (5-ASA) (or a salt or an ester thereof) and a physiologically acceptable first helper ingredient, preferably a cellulose derivative, in particular microcrystalline cellulose, and a coating confining said core, said coating comprising a second helper ingredient, preferably a semipermeable polymer, in particular, ethylcellulose; and the majority of the granules, preferably more than 80%, more preferably more than 90%, of the granules being essentially spherical as defined by an aspect ratio within 1.00–1.25, preferably within 1.00–1.20, more preferably within 1.00–1.15; and the majority of the granules, preferably more than 70%, more preferably more than 90%, of the granules of the composition exerting sieve values in the range of 0.5 mm–2.0 mm, preferably in the range of 0.7 mm–1.1 mm; and the composition exerting the following in vitro dissolution rates [when measured in a model system using simulated intestinal fluid in USP Paddle System 2 operated at 37° C. with stirring speed 100 rpm]:

a) within 2–20%, preferably within 5–15%, of the total 5-ASA is released after 15 minutes in the model system;

b) within 20–50%, preferably within 25–45%, of the total 5-ASA is released after 60 minutes in the model system;

c) within 30–70%, preferably within 40–60% of the total 5-ASA is released after 90 minutes in the model system;

d) within 50–90%, preferably within 55–80%, of the total 5-ASA is released after 150 minutes in the model system;

e) within 75–100% of the total 5-ASA is released after 240 minutes in the model system.

In the present context "5-ASA" is used as also encompassing pharmaceutically acceptable salts and esters thereof.

The salts of 5-ASA may be acid addition salts, in particular the hydrochloride, but any pharmaceutically acceptable, non-toxic organic or inorganic acid may be used.

Also salts formed with the catboxylic acid group may be used. As examples may be mentioned alkali metal salts (K, Na), alkaline earth metal salts (Ca, Mg), but again any pharmaceutically acceptable, non-toxic salt may be used. The Na- and Ca-salts are preferred.

Applicable esters are e.g.

straight chain or branched $C_1$–$C_{18}$ alkyl esters, e.g. methyl, ethyl, propyl, isopropyl, butyl, isobutyl, amyl, hexyl, heptyl, octyl, nonyl, decyl, lauryl, myristyl, cetyl, and stearyl, etc., straight chain or branched $C_2$–$C_{18}$ alkenyl esters, e.g. vinyl, allyl, undecenyl, oleyl, linolenyl, etc., $C_3$–$C_8$ cycloalkyl esters, e.g. cyclopropyl, cyclobutyl, cyclopentyl, cyclohexyl, cycloheptyl and cyclooctyl, etc., aryl esters, e.g. phenyl, toluyl, xylyl, naphthyl, etc., alicyclic esters, e.g. menthyl, etc., or aralkyl esters, e.g. benzyl, phenethyl, etc.

DETAILED DESCRIPTION OF THE INVENTION

The present invention provides for an oral composition in the form of granules designed for direct oral administration, i.e. the granules satisfy the pharmaceutical requirements without being formulated e.g. as tablets or e.g. formulated in capsules.

Specific problems had to be overcome, first of all the individual granules should be able to pass relatively quickly through the ventricle without any significant dissolution of 5-ASA, and subsequently a fraction of the 5-ASA should be distributed both in the small and large intestine and reside there in sufficient time for exerting the localized effect.

The present invention provides a modified release oral composition for the treatment of inflammatory bowel diseases, said composition ensuring bio-availability of 5-aminosalicylic acid (5-ASA) in both the small and large intestine, and comprising:

individually coated granules, each granule comprising:

a core comprising 5-aminosalicylic acid (5-ASA) or a pharmaceutically acceptable salt or ester thereof and a physiologically acceptable first helper ingredient, preferably a cellulose derivative, in particular microcrystalline cellulose, and a coating confining said core, said coating comprising a second helper ingredient, preferably a semipermeable polymer, in particular ethylcellulose; and the majority of the granules, preferably more than 80%, more preferably more than 90%, of the granules being essentially spherical as defined by an aspect ratio within 1.0–1.25, preferably within 1.00–1.20, more preferably within 1.00–1.15; and the majority of the granules, preferably more than 70%, more preferably more than 90%, of the granules of the composition exerting sieve values in the range of 0.5 mm–2.0 mm, preferably in the range of 0.7 mm–1.1 mm; and the composition exerting the following in vitro dissolution rates [when measured in a model system using simulated intestinal fluid in USP Paddle System 2 operated at 37° C. with stirring speed 100 rpm]:

a) within 2–20%, preferably within 5–15%, of the total 5-ASA is released after 15 minutes in the model system;

b) within 20–50%, preferably within 25–45%, of the total 5-ASA is released after 60 minutes in the model system;

c) within 30–70%, preferably within 40–60% of the total 5-ASA is released after 90 minutes in the model system;

d) within 50–90%, preferably within 55–80%, of the total 5-ASA is released after 150 minutes in the model system;

e) within 75–100% of the total 5-ASA is released after 240 minutes in the model system.

In the present context "first helper ingredient" is a spheronization aid, preferably microcrystalline cellulose. A "second helper ingredient" is a coating material which preferably acts as a diffusion-rate limiting barrier, but may also act as erodable, degradable rate-limiting barrier. The preferred ingredient is ethylcellulose.

The composition or the invention exerts the following in vivo 5-ASA release parameters:

provided the gastric emptying is within the normal range, 50% of the granules have left the stomach within 60 minutes after intake of the composition, preferably within 30 minutes.

Furthermore, the composition exerts the following in viva 5-ASA release parameters:

provided the small bowel transit time is within the normal range, 50% of the granules is present in the small bowel 3–6 hours after intake of the composition.

Furthermore, the composition exerts the following in vivo 5-ASA release parameters:

provided the large bowel transit time is within the normal range, 50% of the granules is present in the large bowel 12–50 hours after intake of the composition.

The transit time of various pharmaceutical formulations has been the subject of numerous studies.

Bechgaard, H., Acta Pharmaceutica Technologica 28(2), 1982, studied the critical factors influencing gastrointestinal absorption and focused on the gastrointestinal transit time and pH. She pointed to the marked difference in transit time between single-unit dosages, i.e. oral pharmaceutical formulations consisting of one non-disintegrating unit and multiple-unit dosage, i.e. oral pharmaceutical formulations consisting of a unit which disintegrates in the stomach into a large number of sub-units.

For single-unit dosage forms Bechgaard reports gastric emptying in the range from 0 to 24 hours, while the most recent studies cited (Bogentoft et al.) for multiple-unit dosage forms varies from 1.5 to 2.5 hours in fasting condition to 2.3 to 3 hours in non-fasting condition.

Bechgaard does not report overall intestinal transit time but only the transit time from mouth to caecum. Again there is a very considerable variation for single-unit dosages ranging from 5 to 40 hours, while the transit time for multiple units lie within a more narrow range. Bechgaard obtained results showing a large variation as a function of the density of the pellets, which, however, could not be verified by Bogentoft (6,1±0,9 to 7,1±0,8 hours).

The Pentasa® formulation according to the above-mentioned U.S. patents is a multiple unit formulation and the release of 5-ASA from Pentasa during normal and accelerated intestinal transit time in 7 healthy volunteers has been investigated by Christensen, L. A. et al., Br, J. Clin. Pharmac. (1987), 23, 365–369.

Daily dose was 1500 Pentasa, normal transit time (NTT) was 24 h (16–26 h) and accelerated transit time (ATT), caused by a laxative, was 5 h (4–9 h). Median total recovery (24 h, 4-ASA+acetyl-5-ASA) was 87% (61–129%) (NTT) and 81% (56–100%) (ATT), respectively, (P>0.10). An almost complete release of 5-ASA from Pentasa takes place during NTT. At ATT conditions about 88% is released, indicating Pentasa to be an acceptable source of 5-ASA also in diarrhoeal states.

While only a relatively small group of volunteers were investigated 6 of the volunteers had NTT's in the range from 24 to 26 hours and 1 had an NTT of 16 hours.

The pH-profile and regional transit times of the normal gut has been measured by a radiotelemetry device by F ällingborg, J., et al., Aliment. Pharmacol. therap. (1989) 3,605–613. The pH of the gut lumen was measured in 39 healthy persons using a pH-sensitive, radiotransmitting capsule. Thirteen persons were studied twice. The location of the capsule was determined by X-ray. The pH rose from 6.4 in the duodenum to 7.3 in the distal part of the small intestine. In 17 persons the pH dropped by 0.1–0.8 pH units during the last hours of the small intestinal transit. The pH was 5.7 in the caecum, but rose to 6.6 in the rectum. Gastric residence time was 1.1 h, small intestinal transit was 8 h, and colonic transit time was 17.5 h (median values). The results provide a firmer basis for prediction of the level, and the rate of release of active substance from pH-dependent sustained-release oral preparations and confirm the data obtained by Christensen op.cit.

Further advantages of the composition of the invention are related to improvements with respect to compliance and reproducibility of pharmaceutical characteristics, including laboratory characteristics, especially reproducibility of coating technique parameters.

DESCRIPTION OF THE MANUFACTURING PROCESS

5-ASA and the first helper ingredient are weighed out in the predetermined ratio, e.g. wherein the % by weight of 5-ASA of the total weight of said granule ranging from 30–90%, preferably from 40–80%, more preferably from 50–60%, most preferably about 50%.

The ingredients are thoroughly mixed in a mixing container.

The next step is a granulating process comprising mixing the ingredients with a granulating agent, preferably water, e.g. in the range of 70–90% by weight of the water of the total amount of 5-ASA and helper ingredients. Preferably the granulation is carried out in the mixing container.

An advantage of this step of the process is that it may be performed with water, thus avoiding using organic solvents.

In a subsequent step, an extrusion may be performed by extruding the above-mentioned mixture through sieves with pores of a diameter of e.g. 1.0 mm.

The subsequent step involves spheronization of the mixture by applying the mixture on a spheronizing apparatus, preferably a NICA spheronizer. The process is carefully monitored, and the speed and the employed time interval adjusted according to the instructions of the apparatus, e.g. operated at the maximally allowed speed, and so as to obtain the size and shape of the 5-ASA granules as specified herein.

After the spheronizing step, the granules are transferred to a fluid-bed drying system, and after drying, the granules are individually coated with the second helper ingredient, preferably ethylcellulose, said helper ingredient being dissolved in e.g. an organic solvent, preferably acetone, in particular in a concentration of from 0.1–5% w/w.

The monitoring of the obtainment of granules having the specified shapes and sizes may be performed by the following procedure:

I. Image processing and analysis:

A commercially available microscope and analysis software was obtained from Leica ("Leica Q500MC Image Analysis System") and was used to determine the dimensions and the aspect ratio of the prepared granules.

The aspect ratio as used herein is defined as the ratio of the length divided by the breadth. The length is defined as the length of the longest dimension of the granule. The breadth is defined as the length of the shortest dimension of the granule.

Samples were taken up randomly, e.g. in triplicate.

The compositions according to the invention should meet the following criteria:

the majority of the granules, preferably more than 80%, more preferably more than 90%, of the granules are essentially spherical as defined by an aspect ratio within 1.00–1.25, preferably within 1.00–1.20, more preferably within 1.00–1.15.

II. Furthermore, the particle size distribution of the granules of the composition can be determined by the LEICA ANALYSIS SYSTEM as described above, and also in the following way:

Representative samples of a granule preparation are sieved over a sieve-stack of varying sieves, using fixed time and oscillation, the sieves typically being:

1.40 mm–1.25 mm–1.12 mm–1.00 mm–0.710 mm–0.50 mm–0.355 mm–0.250 mm.

The compositions according to the invention should meet the following criteria:

the majority of the granules, preferably more than 70%, more preferably more than 90%, of the granules of the composition exerting sieve values in the range of 0.5 mm–2.0 mm, preferably in the range of 0.7 mm–1.1 mm.

Furthermore, the prepared granule preparations are tested in an in vitro model system for dissolution profiles and using simulated intestinal fluid, 0.1 M Na phosphate buffer, pH 7.5, in USP Paddle System 2 operated at 37° C. with stirring speed 100 rpm. Batches exerting the dissolution profiles described below are selected for clinical purposes. The preferred dissolution profiles of the granules of the invention are as follows:

a) within 2–20%, preferably within 5–15%, of the total 5-ASA is released after 15 minutes in the model system;

b) within 20–50%, preferably within 25–45% of the total 5-ASA is released after 60 minutes in the model system;

c) within 30–70%, preferably within 40–60% of the total 5-ASA is released after 90 minutes in the model system;

d) within 50–90%, preferably within 55–80%, of the total 5-ASA is released after 150 minutes in the model system;

e) within 75–100% of the total 5-ASA is released after 240 minutes in the model system.

DETAILED DESCRIPTION OF THE GEOMETRICAL/STRUCTURAL CHARACTERISTICS OF THE GRANULES

Granules or the invention are selected so as to exert the following geometrical/structural characteristics:

the majority of the granules, preferably mote than 80%, more preferably more than 90%, of the granules being essentially spherical as defined by an aspect ratio within 1.00–1.25, preferably within 1.00–1.20, more preferably within 1.00–1.15; and the majority of the granules, preferably more than 70%, more preferably more than 90%, of the granules of the composition exerting sieve values in the range of 0.5 mm–2.0 mm, preferably in the range of 0.7 mm–1.1 mm.

PREFERRED EMBODIMENT OF THE INVENTION (BATCH 322202)—see FIG. 2

For preferred granules according to the invention, the following results were obtained (measurements based on 75 measurements on granules obtained by random sampling)

Length

With respect to the length of the granule as defined herein as the length of the longest dimension of the granule, the following values were obtained:

Minimum=0.751 mm–maximum=1.101 mm, i.e. the range was from 0.75 to 1.10 mm.

The granules showed length values varying within (mean±1 SD): 0.881 mm±0.068 mm=from 0.813 mm to 0.949 mm–and the granules had maximal length varying within mean±2 SD: 0.881 mm±0.136 mm=from 0.745 mm to 1.017 mm. Thus, the majority (95%) of the granules showed a length (the length of the longest dimension) of from 0.75 mm to 1.02 mm.

Breadth

With respect to the breadth of the granules defined herein as the length of the shortest dimension of the granule, the following values were obtained:

Minimum=0.674 mm–maximum=0.920 mm, i.e. the range was from 0.67 to 0.92 mm.

The granules had breadth values varying within (mean±1 SD): 0.800 mm±0.058 mm=from 0.742 mm to 0.858 mm–and within (mean±2 SD): 0.800 mm±0.116 mm=from 0.684 mm to 0.916 mm. As seen, the majority 95%) of the granules showed breadth (the length of the shortest dimension) of from 0.68 mm to 0.92 mm.

Aspect Ratio

With respect to the aspect ratio defined herein as the ratio or the length divided by the breadth, (the length being defined as the length of the longest dimension of the granule, and the breadth being defined as the length of the shortest dimension or the granule), the following values were obtained:

Minimum=1.029–maximum=1.250 i.e. the range of aspects ratios was from 1.03 to 1.25.

The granules showed aspect ratios varying within (mean±1 SD): 1.102±0.044=from 1.058 to 1.146–and within (mean±2 SD):=1.102±0.088 mm=from 1.014 to 1.190. As seen, the majority, 97%) of the granules showed aspect ratios of from 1.01 to 1.19.

PREFERRED EMBODIMENT OF THE INVENTION (BATCH 437601)—see FIG. 4

For preferred granules according to the invention, the following results were obtained (measurements based on 75 measurements on granules obtained by random sampling)

Length

With respect to the length of the granule as defined herein as the length of the longest dimension of the granule, the following values were obtained:

Minimum=0.712mm–maximum=1.010 mm, i.e. the range was from 0.71 to 1.01 mm.

The granules had length values varying within (mean±1 SD): 0.834 mm±0.070mm=from 0.764 mm to 0.904 mm; and within (mean±2 SD); 0.834 mm±0.140 mm=from 0.694 mm to 0.974 mm. As seen, the majority, 98%) of the granules showed a length (the length of longest dimension) of from 0.69 mm to 1.02 mm.

Breadth

With respect to the breadth of the granules defined herein as the length of the shortest dimension of the granule, the following values were obtained:

Minimum=0.648 mm–maximum=0.907 mm, i.e. the range wag from 0.65 to 0.91 mm.

The granules had breadth values varying within (mean±1 SD):=0.759 mm±0.069 mm=from 0.690 mm to 0.828 mm; and within (mean±2 SD): 0.759 mm±0.138 mm–from 0.621 mm to 0.897 mm. As seen, the majority, 95%) of the granules showed breadth (the length of the shortest dimension) of from 0.62 mm to 0.90 mm.

Aspect Ratio

With respect to the aspect ratio defined herein as the ratio of the length divided by the breadth, (the length being defined as the length of the longest dimension of the granule, and the breadth being defined as the length of the shortest dimension of the granule), the following values were obtained:

Minimum=1.016–maximum=1.266 i.e, the range of aspects ratios was from 1.02 to 1.27.

The granules showed aspect ratios varying within (mean±1 SD): 1.100±0.046=from 1.054 to 1.146; and within (mean±2 SD): 1.100±0.092 mm=from 1.008 to 1.192. As seen, the majority (approx. 95%) of the granules showed aspect ratios of from 1.01 to 1.19.

Treatment of Inflammatory Bowel Diseases

A main aspect of the invention is a method for the treatment of inflammatory bowel diseases (IBD) in particular Crohn's disease, colitis ulcerosa, an unclassified form of said diseases, or a diagnosed subtype of said disease comprising orally administering a pharmacologically effective amount of the composition according to the invention.

The term "pharmacologically effective amount" as used herein, represents an amount of a compound of the invention which is capable of inducing the desired therapeutical effect in the individual in need thereof. The particular dose of 5-ASA administered according to the present invention will, of course, be determined by the particular circumstances relating to the case, including the particular condition and pathological site to be treated, the sex, age, and weight of the individual, and similar considerations.

The present invention is also useful in a maintenance treatment of more or less chronic inflammatory bowel disease, inter alia because systemic effects and other adverse effects due to the 5-ASA are negligible. Thus, relatively long treatment cycles employing relatively high total amounts of drugs may be prescribed with the concomitant reduced risk of adverse effects.

The target part of the gastrointestinal tract is a target part in the proximal small intestine, the mid small intestine, the distal small intestine, the caecum, the ascending colon, the transverse colon, the descending colon, the sigmoid colon and/or the rectum.

An aspect of the invention is a composition, wherein the 5-ASA is in a unit dosage form and comprises 5-ASA in amounts suitable for the administration of from 250 mg to 12 g, preferably from 500 mg to 6 g, more preferably from 500 mg to 4 g, e.g. in unit dosage form each comprising 500 mg, 1 g, 2 g, 5 g, or 6 g.

The term "unit dosage form" refers to physically discrete units suitable as unitary dosages for clinical use, each unit containing a predetermined quantity of 5-ASA calculated to produce the desired therapeutic effect.

Furthermore, the composition is preferably a composition, wherein the 5-ASA is supplied as a unit dosage forms in sealed packages to be opened immediately prior to use, e.g. sachets or sticks

BRIEF DESCRIPTION OF THE DRAWINGS

FIG. 2 shows the corresponding aspect ratio determinations, obtained by LEICA Q500MC Image Analysis System.

FIGS. 3 and 4 show similar data obtained from another batch.

It is seen that the dissolution profile of the conventional granules are very different from the profiles of the granules of the invention.

Figure 6:
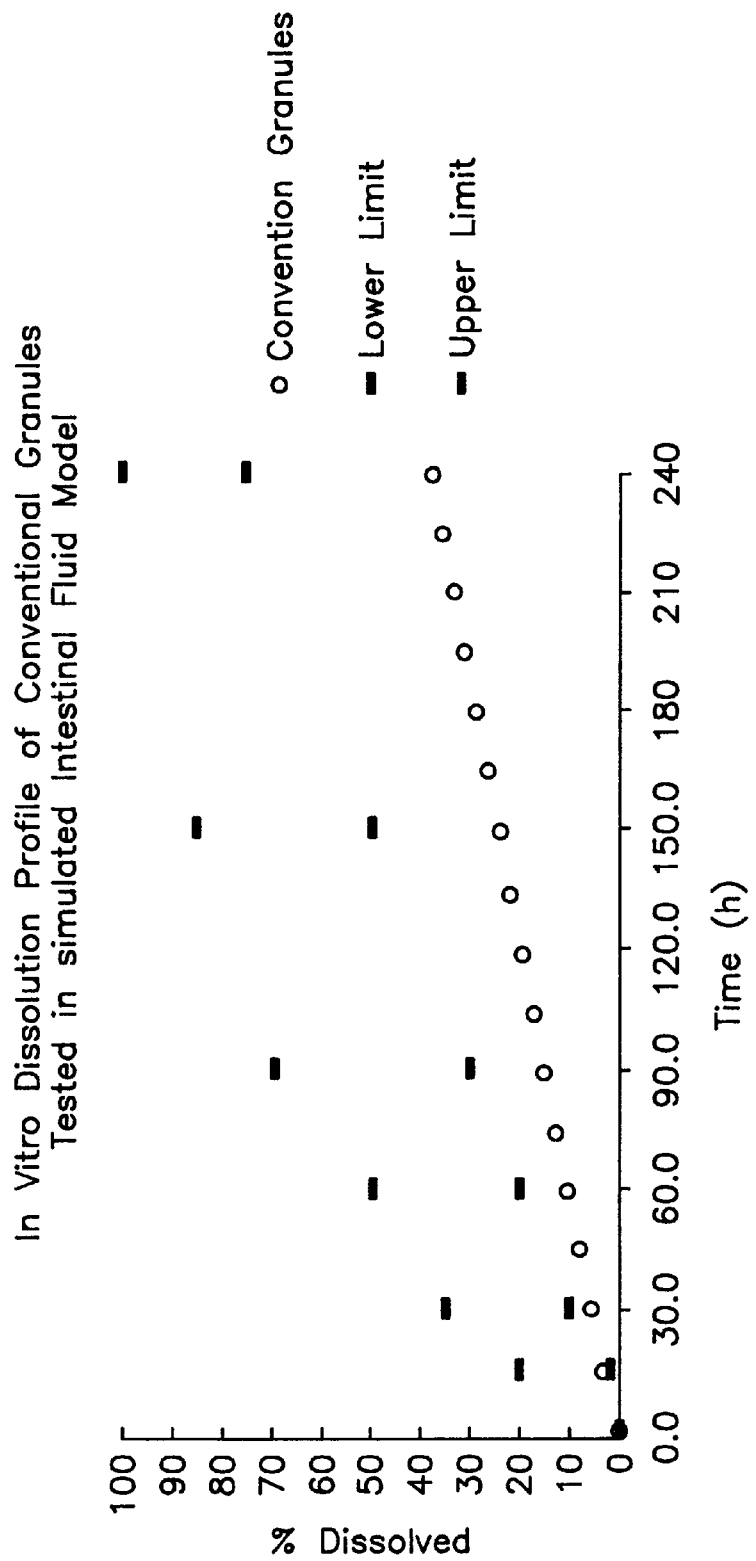
FIG. 6 is a graphical depiction showing the same dissolution rate intervals as in FIG. 5, but also showing data obtained from a comparison experiment.
Figure 7:
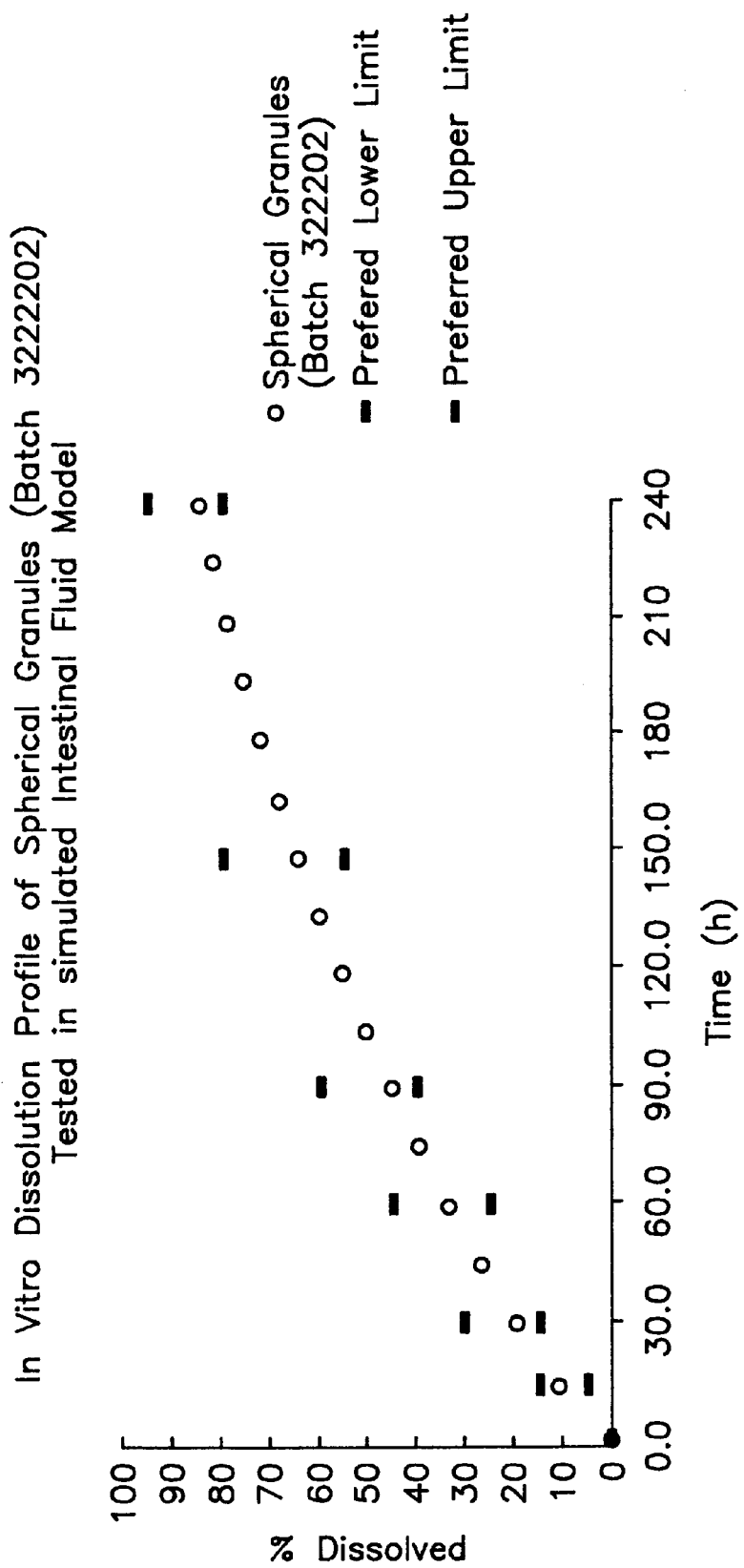

FIG. 7 is a graphical depiction of data obtained from spherical granules of the invention. The test procedure was as in FIG. 6. Results are within the preferred limits.

Figure 8:
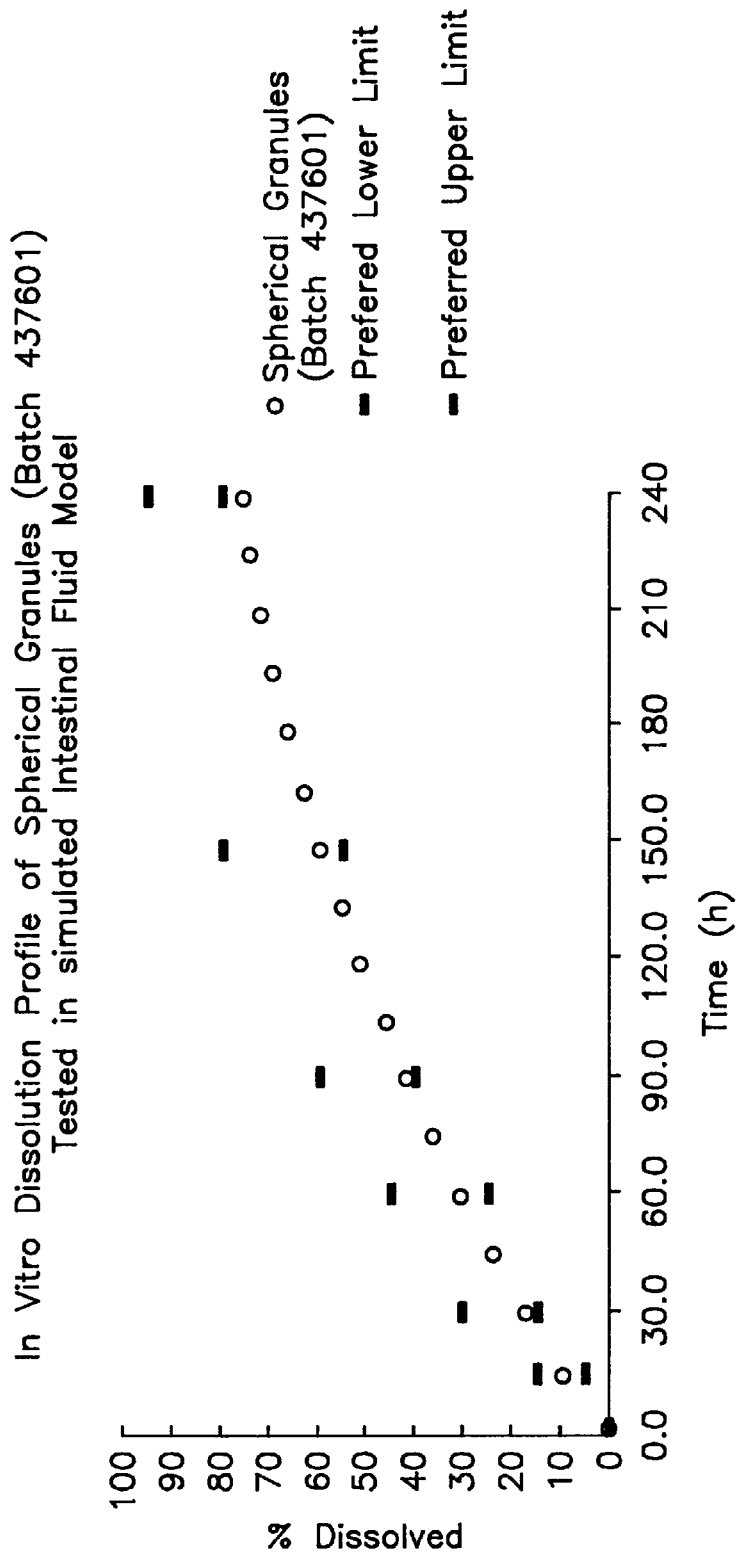

FIG. 8 is a graphical depiction of data obtained from spherical granules of the invention. The test procedure was as in FIG. 6. Results are within the preferred limits.

Figure 9:
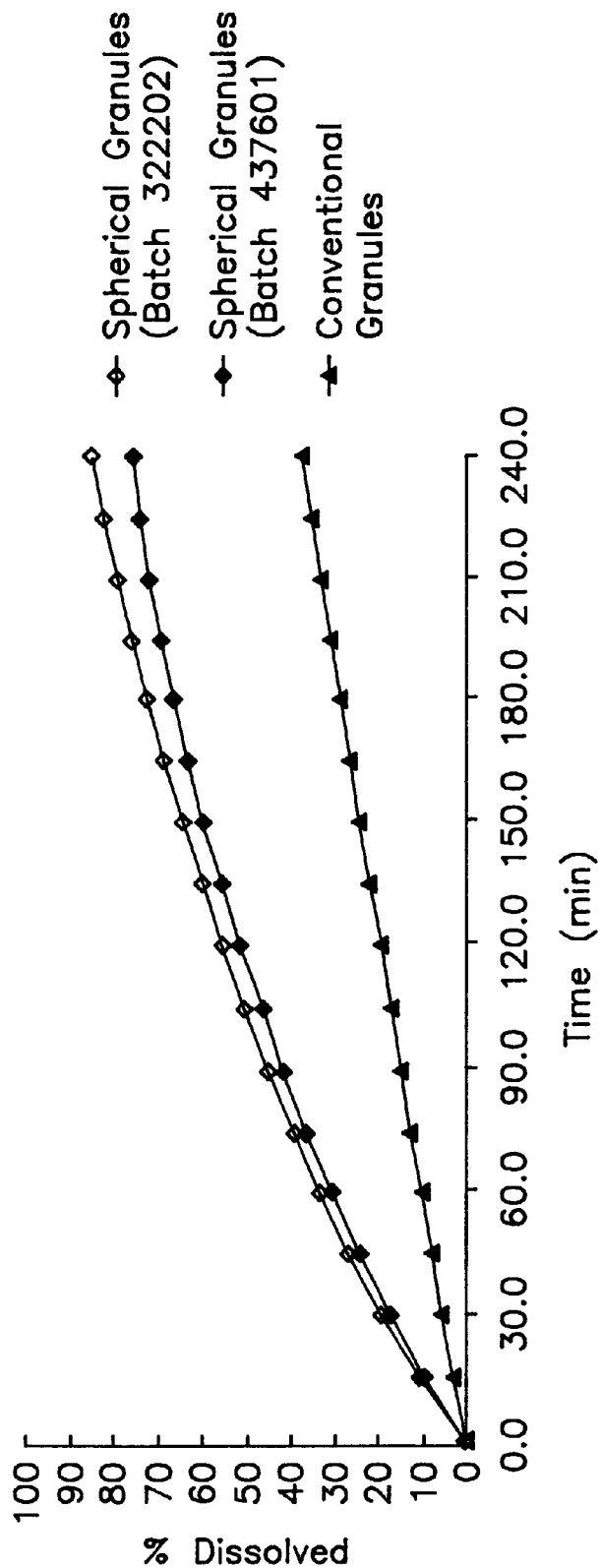

FIG. 9 is a graphical depiction showing the results described in FIGS. 6 an 7 and 8 on the same graph.

FIG. 10 shows a table relating to in vivo gastric emptying time and colon arrival time of spherical granules.

Figure 11:
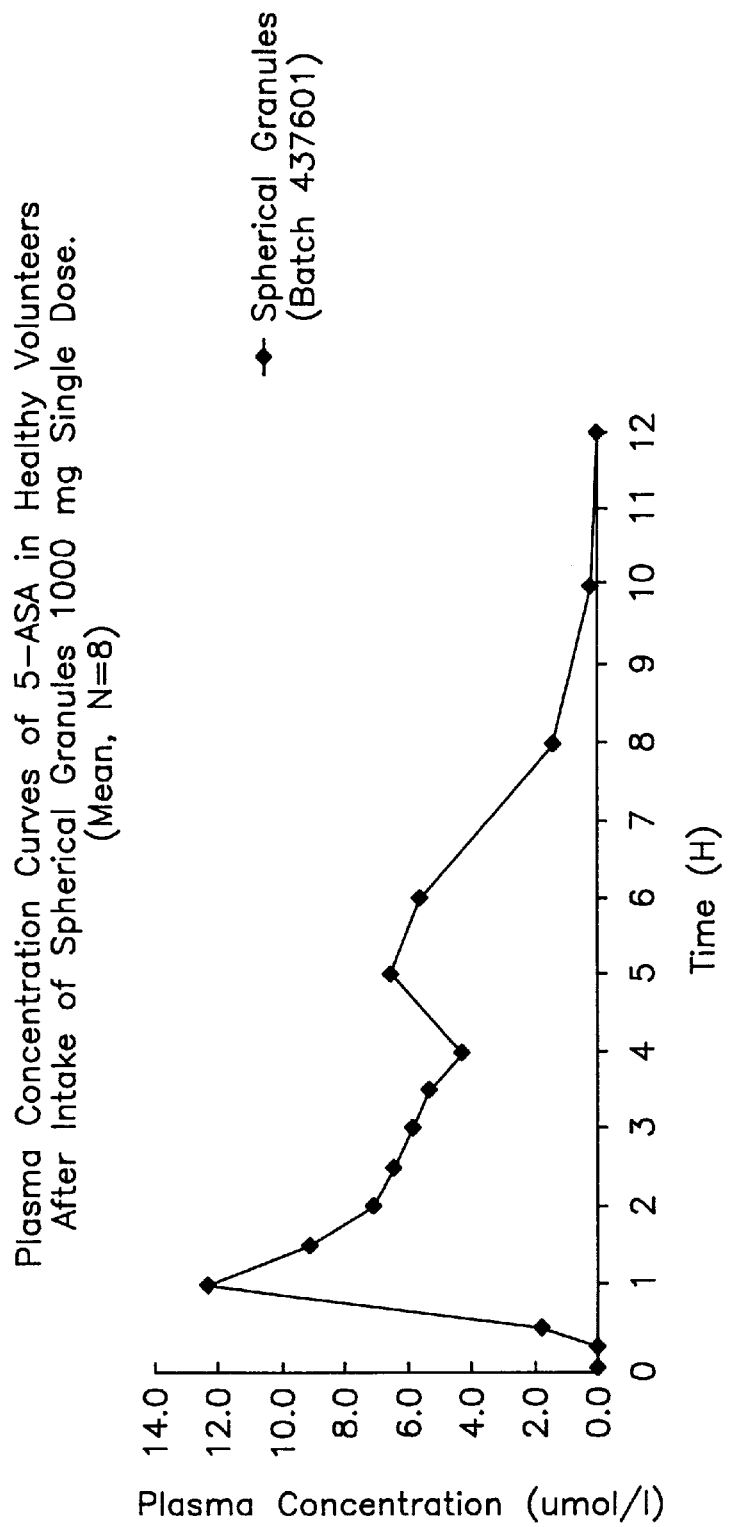
Figure 12:
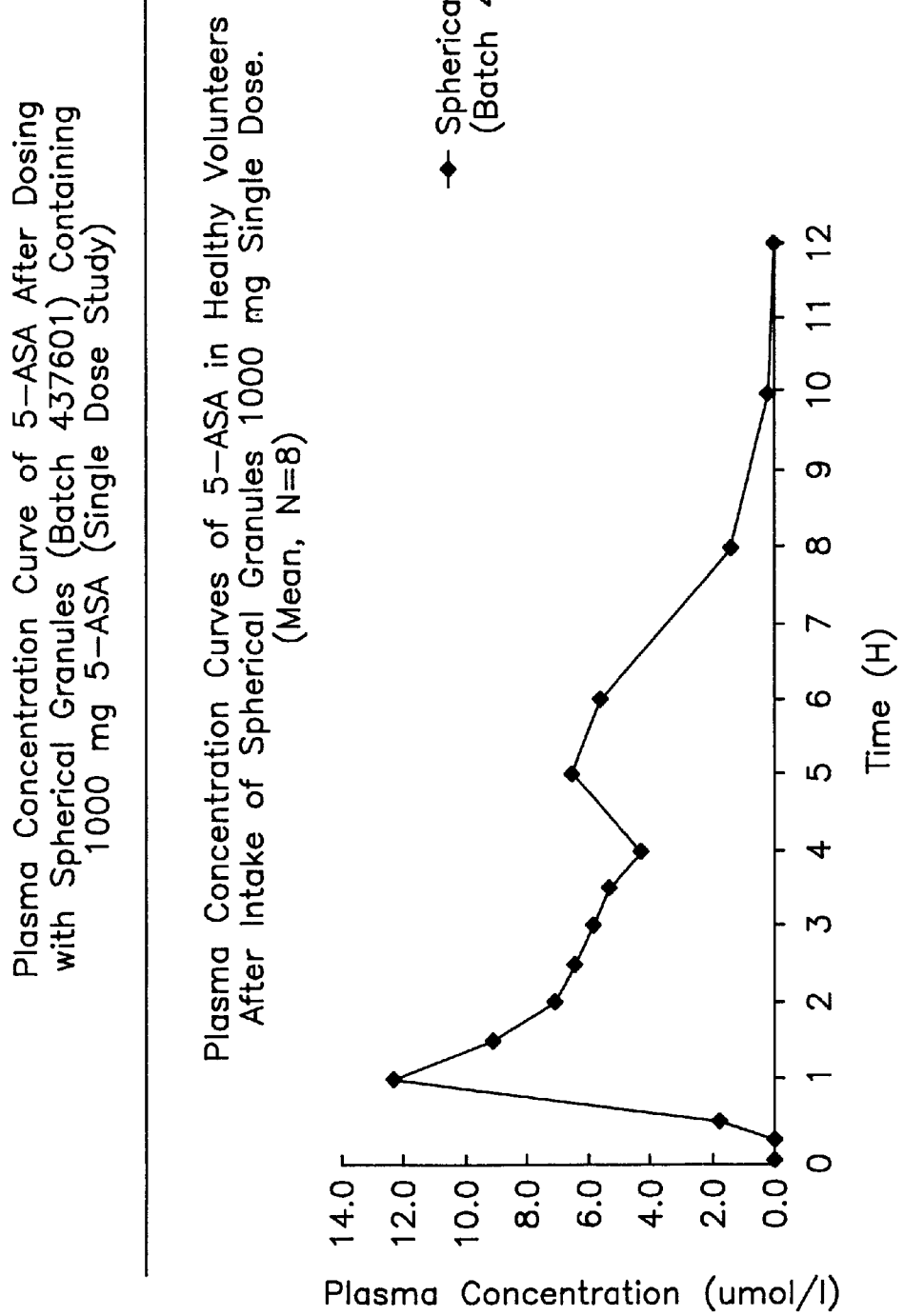

FIG. 11 and FIG. 12 show results from the same clinical study as described in FIG. 10: plasma concentration curves of 5-ASSA.

EXAMPLE 1

The Manufacture of Granule Compositions According to the Invention 5000 g 5-ASA and 5000 g microcrystalline cellulose were weighed out and carefully mixed at a fixed time and speed. 8000 g purified water was poured into the blending container and the ingredients were mixed.

The mixture was extruded through 1.0 mm sieves, and spheronized at fixed time and speed. After carefully monitored spheronization, using maximal speed (790 rpm) of the NICA spheronizing apparatus (NICA S2-450) for a fixed interval of time, e.g. 5 minutes, being adapted to the amount of granule mixture applied to the apparatus, the spheronized granules were transferred to a fluid-bed drying system. After drying, the pellets were spray-coated with ethyl cellulose dissolved in acetone.

Finally, the granules were analyzed and selected as described above, with respect to the geometrical properties.

For determination of the particle size distribution, typically 400 grams of granules were used. The determination was carried out with a Retsch laboratory sieving machine type VIBRO (1.400–1.250–1.120–1.000–0.710–0.500–0.355–0.250 mm). The oscillation amplitude control regulation was set at 60, for 10 minutes.

The specific batches of granules prepared as described above are further characterized by the accompanying drawings.

Description of the Tests and Results

Figure 1:
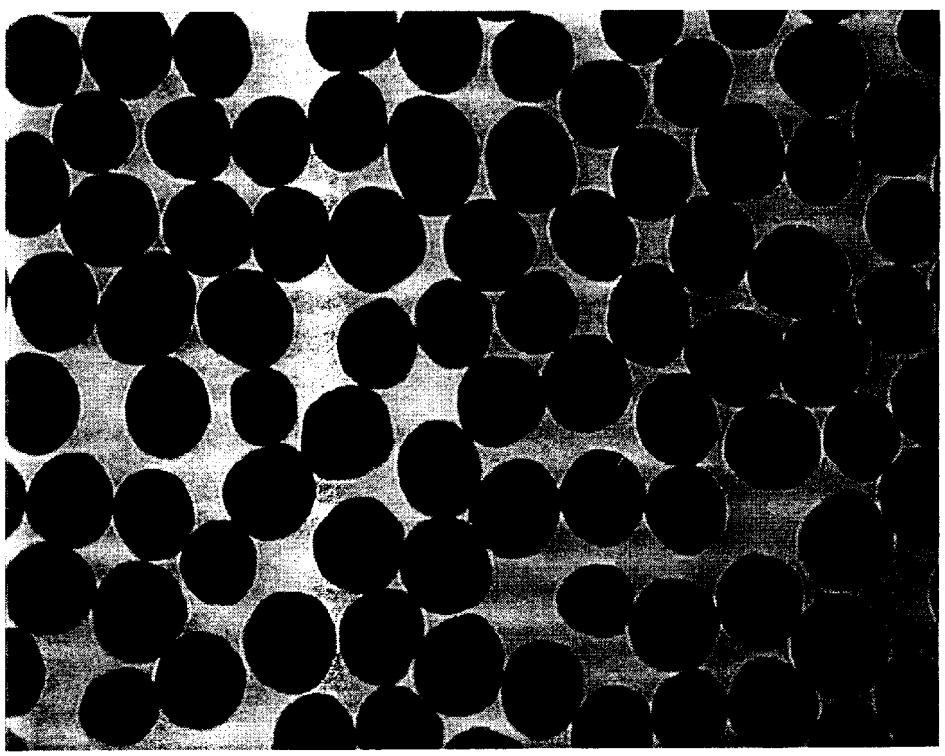
FIG. 1 shows an image analysis of spherical granules of a preferred embodiment of the invention prepared as described below.

An image analysis of spherical granules of a preferred embodiment (batch 322201) of the invention is shown in FIG. 1.

FIG. 2 is a table showing corresponding geometrical characteristics obtained from the same batch, including data representing length, breadth, and aspect ratio determinations—all obtained by the LEICA Q500MC Image Analysis System. Typically approximately 3×300 mg of granules are taken randomly for image processing and analysis.

Figure 3:
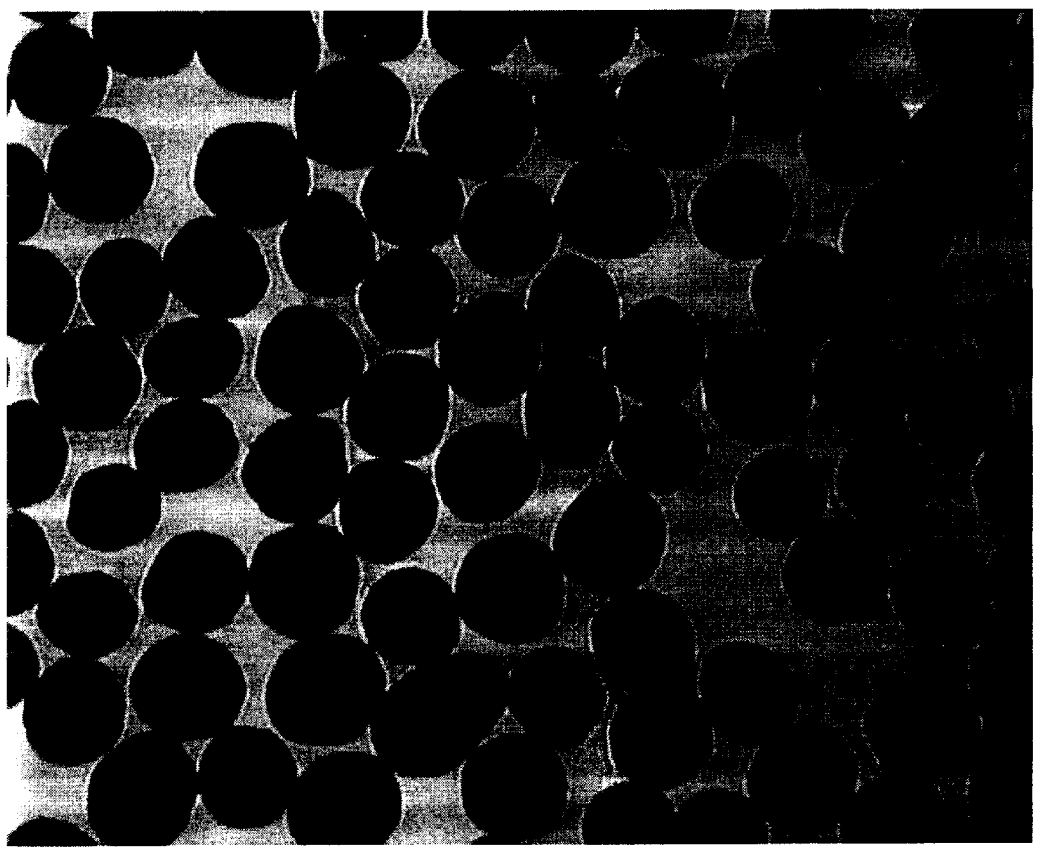

FIGS. 3 and 4 show image analysis and geometrical data obtained from batch 437601.

Test procedure for dissolution rates:

The in vitro dissolution rates were tested in simulated intestinal fluid using a USP Paddle system 2 Dissolution System. The following conditions were applied:

Dissolution Fluid: 0.1 M Na-phosphate buffer pH=7.5
Fluid Volume: 1000 ml
Temperature: 37° C.
Stirring speed: 1.00 rpm A graphical depiction of the preferred dissolution rate intervals of the granules according to the invention is shown in FIG. 5.

Comparison Study

A comparison study was performed using a portion of some granules representing a 5-ASA granulate prepared as an intermediary product prior to the addition of tablet ingredients and compression into (tablets, i.e. an intermediary 5-ASA granulate as prepared prior to the formulation of conventional 5-ASA tablets. The comparison results showed that such "conventional" granules did not provide the properties characteristic of the granules of the present invention. The conventional granules employed in the comparison study were granules made from a homogenous mixture of 5% polyvinylpyrrolidone and 95% 5-ASA, and granulated and extruded (1.0 mm sieve), and subsequently coated with ethylcellulose.—6 batches were tested.

Figure 5:
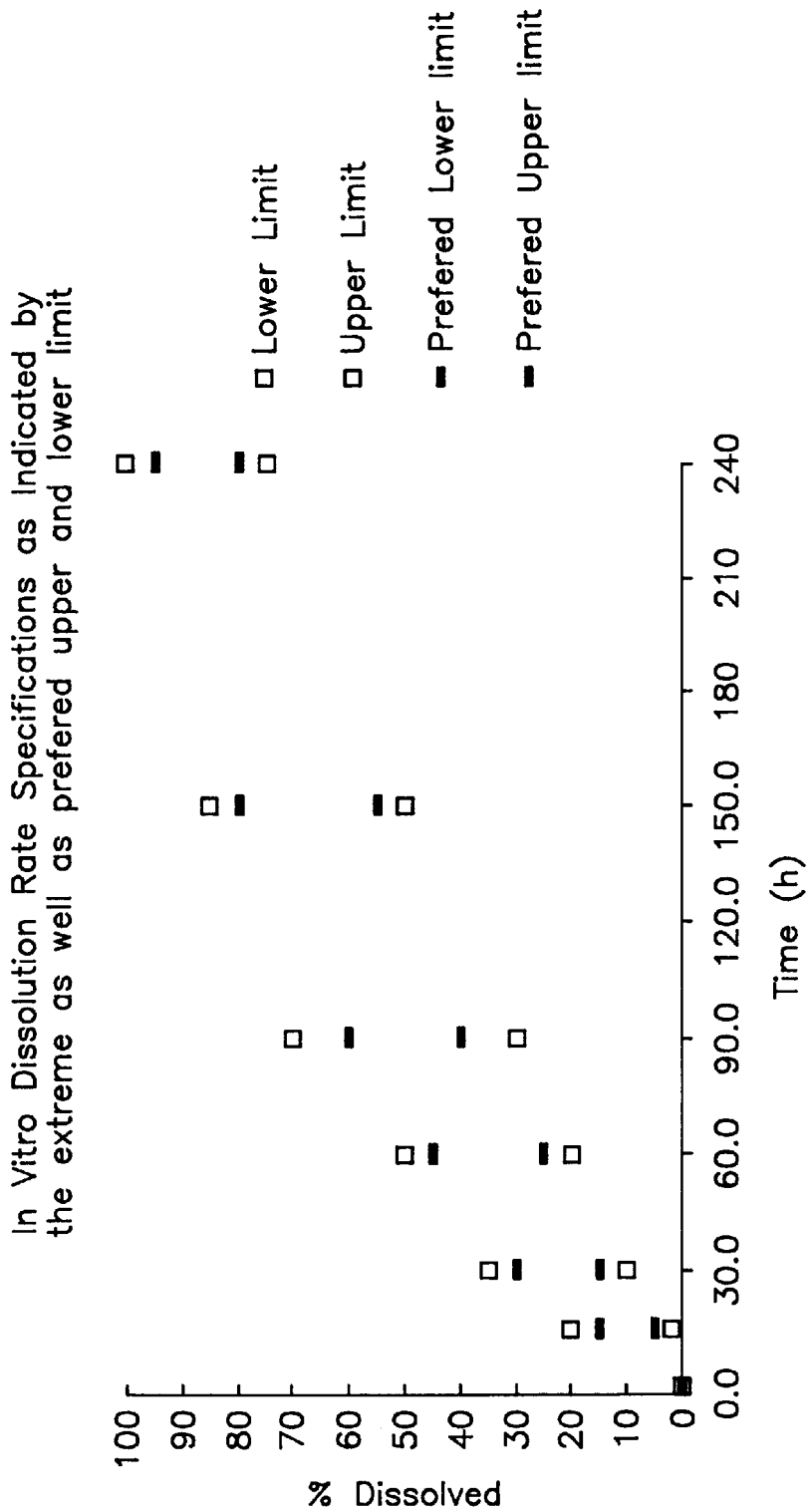
FIG. 5 is a graphical depiction of the preferred dissolution rate intervals of the granules according to the invention.

FIG. 6 is a graphical depiction showing the same dissolution rate intervals as in FIG. 5, but also showing data obtained from a comparison experiment:

It is seen that the dissolution profile of the conventional granules is very different from the profiles of the granules of the invention.

FIG. 7 is a graphical depiction of data obtained from spherical granules of the invention (batch 322202). The test procedure was as in FIG. 6. Results are within the preferred limits.

FIG. 8 is a graphical depiction of data obtained from spherical granules of the invention (batch 437601). The test procedure was as in FIG. 6. Results are within the preferred limits.

FIG. 9 is a graphical depiction showing the results described in FIG. 6 (comparison data) and FIG. 7 and FIG. 8 on the same graph.

Test Procedure In Vivo

The dispositions of spherical granules were investigated in eight healthy volunteers. The experiments were performed according to a Clinical Study Protocol employed at Pharmaceutical Profiles Ltd, Nottingham, UK., using radiolabelled $^{153}$Sm granules for the localization of the position of the disposed composition. The results are shown in FIG. 10, which is a table showing the gastric emptying time and colon arrival time of the tested spherical granules.

FIG. 11 and FIG. 12 show further results from the clinical study: plasma concentration curves of 5-ASA after administration (1000 mg single dose) of the granule composition of the invention.

EXAMPLE 2

The Manufacture of Granule Compositions According to a Preferred Embodiment of the Invention 1. Dry Mixing of Active Component and Excipient 25.000 g 5-ASA and 25.000 g microcrystalline cellulose (Avicel pH 101) were weighed out and loaded into a Fielder PMA 300 High Shear mixer.

The mixer is closed and the ingredients are mixed with the following parameters.

Time: 10 minutes

Impeller speed: 109 rpm
Chopper speed: Set 1
Acceleration: Acc

When the mixing process was finished 6 samples were taken at the top, in the middle and at the bottom of the Fielder PMA 300. The samples size was 1000 mg which equals 500 mg 5-ASA.

Test results:

| Sample | Bottom mg | Middle mg | Top mg |
|---|---|---|---|
| Batch no.: XK 830 | | | |
| 1 | 500 | 497 | 496 |
| 2 | 496 | 497 | 499 |
| 3 | 496 | 497 | 496 |
| 4 | 496 | 497 | 497 |
| 5 | 496 | 497 | 496 |
| 6 | 498 | 498 | 496 |
| Mean | 497 | 497 | 497 |
| SD | 1.7 | 0.6 | 1.3 |
| RSD | 0.3 | 0.1 | 0.3 |
| ±5%(Mean) | 472–522 | 472–522 | 472–522 |
| Batch no.: XK 831 | | | |
| 1 | 516 | 499 | 496 |
| 2 | 495 | 497 | 495 |
| 3 | 495 | 498 | 496 |
| 4 | 495 | 496 | 497 |
| 5 | 497 | 498 | 497 |
| 6 | 495 | 499 | 495 |
| Mean | 499 | 498 | 496 |
| SD | 8.2 | 1.0 | 0.8 |
| RSD | 1.6 | 0.2 | 0.2 |
| ±5%(Mean) | 474–524 | 473–523 | 471–521 |
| Batch no.: XK 832 | | | |
| 1 | 481 | 478 | 446 |
| 2 | 483 | 478 | 474 |
| 3 | 481 | 478 | 473 |
| 4 | 506 | 476 | 496 |
| 5 | 478 | 475 | 499 |
| 6 | 478 | 475 | 495 |
| Mean | 485 | 477 | 480 |
| SD | 10.7 | 1.3 | 20.3 |
| RSD | 2.2 | 0.3 | 4.2 |
| ±5%(Mean) | 461–509 | 453–501 | 456–504 |

All individual values are within ±5% of group mean and RSD for the three bathes are less than 6%.

The mean of the 6 samples taken at the bottom, in the middle and at the top of the three batches are within ±5% of the theoretical value (500 mg 5-ASA).

2. Wet Mixing

The granulation liquid (42,000 g purified water) was weighed out in a special container and through a valve in the lid of the Fielder PMA 300 the water was loaded into the blending tank.

While adding the water the ingredients are mixed with the following parameters:

| Valve on container: | 3 |
|---|---|
| Time: | 5 minutes |
| Impeller speed: | 109 rpm |
| Chopper speed: | Set 1 |
| Acceleration: | Acc |

When all the water was loaded into the Fielder PMA 300 the ingredients were mixed 4 times with the following parameters:

| | |
|---|---|
| Time: | 5 minutes |
| Impeller speed: | 109 rpm |
| Chopper speed: | Set 0 |
| Acceleration: | Acc |

In the final run the chopper was set on 1 for the last 30 seconds in order to chop agglomerates in the wet mass.

Between each run the lid on the Fielder PMA 300 is opened and the side of the blending tank was scraped clean.

When the mixing process was finished 6 samples were taken at the top, in the middle and at the bottom of the fielder PMA 300. The sample size was 4 grams.

The amount of water in the granules is determined as loss on drying. Loss on drying is the loss of mass expressed as per cent w/w.

The loss on drying is determined using a Mettler LP 16 Infrared Dryer and LJ 16 Moisture Analyzer, 3.0 grams of the sample is placed in the oven and the sample is dried 6 minutes at 105° C. to constant mass. The mean loss on drying for the six samples must be between 43.6% and 48.2%.

Calculation: W %–("Loss on drying"×100)/sample weight.

Test results:
Loss on drying

| Sample | Bottom % | Middle % | Top % |
|---|---|---|---|
| Batch no.: XK 830 | | | |
| 1 | 45.8 | 46.4 | 46.0 |
| 2 | 46.7 | 46.7 | 46.9 |
| 3 | 46.8 | 46.9 | 46.8 |
| 4 | 46.3 | 46.5 | 46.7 |
| 5 | 46.4 | 46.3 | 46.3 |
| 6 | 46.3 | 46.6 | 47.0 |
| Mean | 46.4 | 46.6 | 46.6 |
| SD | 0.4 | 0.2 | 0.4 |
| Batch no.: XK 831 | | | |
| 1 | 46.9 | 46.4 | 46.6 |
| 2 | 45.4 | 46.3 | 47.0 |
| 3 | 46.8 | 46.5 | 47.0 |
| 4 | 46.8 | 46.9 | 46.7 |
| 5 | 46.7 | 47.0 | 47.3 |
| 6 | 47.0 | 46.8 | 46.9 |
| Mean | 46.6 | 46.7 | 46.9 |
| SD | 0.6 | 0.3 | 0.2 |
| Batch no.: XK 832 | | | |
| 1 | 45.9 | 46.9 | 46.2 |
| 2 | 46.1 | 46.3 | 46.5 |
| 3 | 47.1 | 46.4 | 46.6 |
| 4 | 46.2 | 46.7 | 46.2 |
| 5 | 46.5 | 46.7 | 46.7 |
| 6 | 46.5 | 47.0 | 46.7 |
| Mean | 46.4 | 46.7 | 46.5 |
| SD | 0.4 | 0.3 | 0.2 |

The mean loss on drying of the 6 samples taken at the bottom, in the middle and at the top of the three batches is between 45.6% and 47.3%.

An even distribution of the granulation liquid is obtained, i.e. the standard deviation is very low.

3. Extrusion and Spheronization of the Pellets

The resulting granules (91,300 g) are transferred to the extruder/spheronized (Nica system 623-006 extruder/Nica system 610-006 spheronizer) and the wet mass was extruded with fixed feeder and extruder speed. The extruder mass was automatically loaded onto the spheronizer and the mass was spheronized a fixed time on the plate.

| | |
|---|---|
| Speed feeder: | 20 rpm |
| Speed extruder: | 50 rpm |
| Extrusion time: | 150 seconds |
| Speed spheronizer: | 400 rpm |
| Spheronization time: | 300 seconds |

Just after the pellets from each run of the spheronization process have been discarded from the spheronizer 1000 g of pellets are taken for analysis.

The wet spheronized pellets are transferred to the STREA fluid-bed drying system for drying.

| | | |
|---|---|---|
| Drying parameters: | Drying temperature: | 60° C. |
| | Capacity of the fan: | max |
| | Drying time: | 35 min. |

The outlet air temperature is recorded and the pellets are dry when this temperature is >55° C. For determination of the particle size distribution 400 grams of pellets are used. The determination is carried out using a Retsch laboratory sieving machine type VIBRO. The oscillation amplitude control set at 60 for 10 minutes. The following sieves are used:

1.4 mm, 1.25 mm, 1.12 mm, 1.0 mm, 0.710 mm, 0.5 mm, 0.35 mm, 0.250 mm.

3×300 mg pellets are taken for image processing and analysis. The analysis includes measurement or length, breadth, perimeter and aspect ratio of the pellets. The aspect ratio is defined as the ratio of the length divided by the breadth.

A picture of the pellets is taken for documentation.

Test results

| Particle size: mm | Run 1 | Run 2 | Run 3 | Run 4 | Run 5 | Run 6 | Run 7 | Run 8 |
|---|---|---|---|---|---|---|---|---|
| | | | Sieve analysis: % Batch no.: XK 830 | | | | | |
| <0.5 | 0.0 | 0.0 | 0.0 | 0.0 | 0.0 | 0.0 | 0.0 | 0.0 |
| 0.5 < x < 0.710 | 0.5 | 0.8 | 1.0 | 1.0 | 1.0 | 0.8 | 0.8 | 0.3 |

-continued

| Particle size: mm | Run 1 | Run 2 | Run 3 | Run 4 | Run 5 | Run 6 | Run 7 | Run 8 |
|---|---|---|---|---|---|---|---|---|
| 0.710 < x < 1.25 | 99.3 | 98.8 | 98.5 | 98.8 | 98.8 | 99.0 | 98.8 | 99.5 |
| >1.25 | 0.0 | 0.0 | 0.3 | 0.3 | 0.3 | 0.3 | 0.3 | 0.0 |
| Σ | 99.8 | 99.5 | 99.8 | 100.0 | 100.0 | 100.0 | 99.8 | 99.8 |
| Sieve analysis: % Batch no.: XK 831 | | | | | | | | |
| <0.5 | 0.0 | 0.0 | 0.0 | 0.0 | 0.0 | 0.0 | 0.0 | 0.0 |
| 0.5 < x < 0.710 | 0.3 | 0.3 | 0.3 | 0.3 | 0.3 | 0.3 | 0.3 | 0.0 |
| 0.710 < x < 1.25 | 99.3 | 99.0 | 99.0 | 99.0 | 98.8 | 99.3 | 99.0 | 99.2 |
| >1.25 | 0.3 | 0.3 | 0.3 | 0.3 | 0.5 | 0.3 | 0.5 | 0.3 |
| Σ | 99.8 | 99.5 | 99.5 | 99.5 | 99.5 | 99.8 | 99.8 | 99.5 |
| Sieve analysis: % Batch no.: XK 832 | | | | | | | | |
| <0.5 | 0.0 | 0.0 | 0.0 | 0.0 | 0.0 | 0.0 | 0.0 | 0.0 |
| 0.5 < x < 0.710 | 0.5 | 0.8 | 1.0 | 1.0 | 1.0 | 1.0 | 0.8 | 0.3 |
| 0.7100 < x < 1.25 | 98.8 | 98.5 | 98.3 | 98.5 | 98.8 | 98.3 | 97.9 | 98.5 |
| >1.25 | 0.3 | 0.5 | 0.3 | 0.3 | 0.3 | 1.0 | 0.8 | 1.32 |
| Σ | 99.5 | 99.8 | 99.5 | 99.8 | 100.0 | 100.3 | 99.5 | 100.0 |

Test results
Image processing and analysis

| Run | Length mm. | SD | Breadth mm. | SD | Perimeter mm. | SD | Aspect Ratio | SD |
|---|---|---|---|---|---|---|---|---|
| Batch no XK 830 | | | | | | | | |
| 1 | 0.894 | 0.085 | 0.779 | 0.069 | 2.769 | 0.288 | 1.083 | 0.175 |
| 2 | 0.866 | 0.072 | 0.765 | 0.062 | 2.667 | 0.202 | 1.050 | 0.025 |
| 3 | 0.872 | 0.079 | 0.767 | 0.071 | 2.717 | 0.296 | 1.090 | 0.218 |
| 4 | 0.879 | 0.060 | 0.771 | 0.072 | 2.724 | 0.223 | 1.103 | 0.373 |
| 5 | 0.867 | 0.085 | 0.769 | 0.068 | 2.670 | 0.236 | 1.047 | 0.027 |
| 6 | 0.883 | 0.082 | 0.779 | 0.074 | 2.750 | 0.289 | 1.085 | 0.207 |
| 7 | 0.882 | 0.059 | 0.776 | 0.063 | 2.736 | 0.228 | 1.071 | 0.154 |
| 8 | 0.849 | 0.058 | 0.773 | 0.049 | 2.648 | 0.158 | 1.039 | 0.015 |
| Batch no XK 831 | | | | | | | | |
| 1 | 0.964 | 0.093 | 0.850 | 0.058 | 2.983 | 0.260 | 1.068 | 0.153 |
| 2 | 0.979 | 0.105 | 0.858 | 0.062 | 3.036 | 0.402 | 1.081 | 0.204 |
| 3 | 0.997 | 0.129 | 0.855 | 0.091 | 3.042 | 0.350 | 1.061 | 0.096 |
| 4 | 0.984 | 0.116 | 0.866 | 0.067 | 3.059 | 0.569 | 1.072 | 0.271 |
| 5 | 0.973 | 0.152 | 0.844 | 0.142 | 3.008 | 0.545 | 1.095 | 0.221 |
| 6 | 0.998 | 0.124 | 0.872 | 0.107 | 3.069 | 0.394 | 1.073 | 0.159 |
| 7 | 0.999 | 0.115 | 0.883 | 0.080 | 3.098 | 0.414 | 1.063 | 0.131 |
| 8 | 0.913 | 0.096 | 0.811 | 0.045 | 2.818 | 0.222 | 1.046 | 0.025 |
| Batch no XK 832 | | | | | | | | |
| 1 | 0.908 | 0.051 | 0.799 | 0.046 | 2.822 | 0.231 | 1.081 | 0.152 |
| 2 | 0.884 | 0.089 | 0.772 | 0.050 | 2.731 | 0.278 | 1.079 | 0.161 |
| 3 | 0.877 | 0.082 | 0.773 | 0.057 | 2.717 | 0.319 | 1.072 | 0.127 |
| 4 | 0.856 | 0.061 | 0.758 | 0.053 | 2.647 | 0.180 | 1.053 | 0.028 |
| 5 | 0.880 | 0.070 | 0.774 | 0.058 | 2.722 | 0.232 | 1.072 | 0.159 |
| 6 | 0.894 | 0.084 | 0.777 | 0.073 | 2.839 | 0.420 | 1.186 | 0.476 |
| 7 | 0.900 | 0.102 | 0.796 | 0.092 | 2.790 | 0.345 | 1.075 | 0.151 |
| 8 | 0.846 | 0.092 | 0.769 | 0.092 | 2.658 | 0.336 | 1.067 | 0.161 |

The sieve analysis shows that in all three batches moire than 97% of the pellets are in range 0.710<x<1.25 mm.

The image analysis shows that each run in the three batches produces equally round pellets, i.e. the aspect ratio does not differ much from one run to another.

In conclusion the extrusion (Nica system 623-006 extruder) and spheronization (Nica system 610-006 spheronizer) procedure, with the specified parameters, produces smooth pellets with a uniform size distribution.

4. Drying of the Pellets

A Niro Aeromatic MP 3/4 fluid-bed drying system was used.

The spheronized pellets were loaded into the Niro Aeromatic MP 3/4 and the drying process was run automatically.

|  | Preheating | Drying | Cooling |
|---|---|---|---|
| Preheater | 0° C. | 0° C. | 0° C. |
| RH% | 0% | 0% | 0% |
| Cooler | 0° C. | 0° C. | 0° C. |
| Drying temp. | 60° C. | 60° C. | 25° C. |
| Product temp. | 60° C. | 60° C. | 25° C. |
| Air flow | 1100 m³/h | 1100 m³/h | 1100 m³/h |
| Outlet temp. | 60° C. | 60° C. | 25° C. |
| Process time | 20 min. | 210 min. | 10 min. |

When the drying process was finished 6 samples were taken at the top, in the middle and at the bottom of the fluid bed. The sample size was 4 grams.

The amount of water in the granules was determined as loss on drying.

Loss on drying is the loss of mass expressed as per cent w/w. The loss on drying was determined using a Mettler LP 16 Infrared Dryer and LJ 16 Moisture Analyzer. 3.0 grams of the sample is placed in the oven and the sample was dried 6 minutes at 105° C. to constant mass. The mean loss on drying for the six samples must be less than 0.8% and all individual values to be within ∓3×SD.

Calculation: W %=("Loss on drying"×100)/sample weight.

Test results:
Loss on drying

| Sample | Bottom % | Middle % | Top % |
|---|---|---|---|
| Batch no.: XK 830 | | | |
| 1 | 0.39 | 0.59 | 0.79 |
| 2 | 0.60 | 0.89 | 0.80 |
| 3 | 0.39 | 0.81 | 0.90 |
| 4 | 0.50 | 0.51 | 0.91 |
| 5 | 0.60 | 0.81 | 0.79 |
| 6 | 0.59 | 0.69 | 0.79 |
| Mean | 0.51 | 0.72 | 0.83 |
| SD | 0.10 | 0.15 | 0.06 |
| ±3 × SD | 0.21–0.81 | 0.27–1.17 | 0.65–1.01 |

-continued

| | Test results: Loss on drying | | |
|---|---|---|---|
| Sample | Bottom % | Middle % | Top % |
| Batch no.: Xk 831 | | | |
| 1 | 0.59 | 0.58 | 0.79 |
| 2 | 0.52 | 0.68 | 0.70 |
| 3 | 0.61 | 0.59 | 0.71 |
| 4 | 0.58 | 0.60 | 0.80 |
| 5 | 0.52 | 0.59 | 0.70 |
| 6 | 0.61 | 0.62 | 0.81 |
| Mean | 0.57 | 0.61 | 0.75 |
| SD | 0.04 | 0.04 | 0.05 |
| ±3 × SD | 0.45–0.69 | 0.49–0.65 | 0.60–0.90 |
| Batch no.: Xk 832 | | | |
| 1 | 0.81 | 0.71 | 0.79 |
| 2 | 0.72 | 0.71 | 0.70 |
| 3 | 0.79 | 0.81 | 0.69 |
| 4 | 0.69 | 0.70 | 0.70 |
| 5 | 0.69 | 0.81 | 0.80 |
| 6 | 0.69 | 0.70 | 0.69 |
| Mean | 0.73 | 0.74 | 0.73 |
| SD | 0.05 | 0.05 | 0.05 |
| ±3 × SD | 0.58–0.88 | 0.59–0.89 | 0.58–0.88 |

The results shows that the mean loss on drying is less than 0.8% and all individual values are within +3×SD.

5. Sieving of the Pellets

When the pellets are dried they are transferred to a Mogensen feeder LM 0204 which is connected to the Allgaier sieve ATS 600/2. The different fractions are collected and weighed. The sieving is stopped when the Allgaier is empty.

From the fraction 0.710<x<1.4 mm a sample of 500 g is taken for sieve analysis.

For determination of the particle size distribution 400 g of pellets are used. The determination is carried out over a Retsch laboratory sieving machine type VIBRO. The oscillation amplitude control set at 60 for 10 minutes. The following sieves are used:

1.4 mm, 12.5 mm, 1.12 mm, 1.0 mm, 0.710 mm, 0.5 mm, 0.35 mm 0.250 mm

| | Test results: Sieve analysis | | |
|---|---|---|---|
| Particle size: mm | XK 830 | XK 831 | XK 832 |
| <0.5 | 0.0 | 0.0 | 0.0 |
| 0.5 < x < 0.710 | 0.3 | 0.0 | 0.0 |
| 0.710 < x < 1.25 | 99.5 | 99.5 | 100.0 |
| 1.25 < x < 1.4 | 0.0 | 0.8 | 0.0 |
| Σ | 99.8 | 100.3 | 100.0 |

The results show that more than 99% of the pellets are in the range 0.710<x<1.25. Less than 1% of the outside this range.

6. Coating of Pellets (Preparation of Coated Pentasa® Sachets)

The coating of batches of 200 kg sieved pellets with dimensions in the range of 0.710 to 1.25 mm are made in a Hüttlin Kugelcoater HKC 400.

The HKC-400 is a "closed-cycle" equipment comprising a spherical coating apparatus in which the product is kept moving by a conditioned stream of hot air.

The pellets (granulates) ate sprayed with coating liquid which consists of a 0.5% solution of ethylcellulose in acetone via nozzles in the lower part of the Kugelcoater.

The conditioned stream of hot air is recycled. Entrained dust is removed by means of a filter following which the air is cooled to at least −15° C. in order to condense entrained acetone vapor.

Three batches of 200 kg of 5-ASA granulates with dimensions in the range of 0.710 to 1.25 mm were coated with 180.9 kg (90.45%) of a 0.5% solution of ethylcellulose in acetone using a spray pressure of 1.5 bar.

An air flow of 4000 m$^3$/h (oxygen content <8%) at a temperature of 42° C. was used during filling, coating and drying of the granulates.

If the temperature drops below a setpoint of 31° C. the spraying is discontinued until the setpoint is reached.

When the desired amount of coating liquid has been introduced a spray of acetone is introduced in order to avoid clogging of the nozzles.

Subsequently the coated granulates are dried until a setpoint of 38° C. has been reached.

The coater is emptied into a container through a gate in the bottom.

The coated pellets are transferred to a Mogensen vibration sieve and the fractions greater than 1.6 mm are discarded.

The dissolution rates for the three coated batches of Pentasa® sachets were tested on a USP paddle system 2 dissolution system as described in example 1.

Ideally the dissolution profile should be 50% after 90 minutes and at least 75% after 240 minutes. An acceptable profile is from 40 to 60% after 90 minutes and at least 75% after 240 minutes.

The three batches were coated under identical conditions and the following dissolution data were determined.

| | | Batch 1 | Batch 2 | Batch 3 | Average | S.D. |
|---|---|---|---|---|---|---|
| 90 min. | Min | 43.53 | 42.44 | 46.57 | | |
| | Max | 45.62 | 57.3 | 49.07 | | |
| | Mean | 44.45 | 53.67 | 47.64 | 48.59 | 3.82 |
| 240 min. | Min | 77.99 | 90.14 | 82.01 | | |
| | Max | 80.41 | 93.3 | 85.23 | | |
| | Mean | 79.13 | 92.15 | 83.76 | 85.01 | 5.39 |

It is seen that all three batches had an acceptable dissolution profile and that the uncoated Pentasa® sachet granulate can be coated to a satisfactory Pentasa® sachet.

We claim:

1. A modified release oral composition for the treatment of inflammatory bowel diseases, said composition ensuring bioavailability of 5-aminosalicylic acid in both the small and large intestine, and consisting essentially of:

individually coated granules, each granule comprising:
 a core consisting essentially of 5-aminosalicylic acid or a pharmaceutically acceptable salt or ester thereof and a physiologically acceptable spheronization aid, and
 a coating confining said core, said coating comprising a rate-limiting barrier material; and the majority of the granules being essentially spherical as defined by an aspect ratio from 1.00–1.25; and the majority of the granules of the composition having sieve values in the range of ≧0.5 mm and <1.4 mm; and the composition having the following in vitro dissolution rates when measured in a model system using simulated intestinal fluid in USP Paddle System 2 operated at 37° C. with a stirring speed of 100 rpm:

a) from 2–20% of the total 5-aminosalicylic acid is released after 15 minutes in the model system;

b) from 20–50% of the total 5-aminosalicylic acid is released after 60 minutes in the model system;
c) from 30–70% of the total 5-aminosalicylic acid is released after 90 minutes in the model system;
d) from 50–90% of the total 5-aminosalicylic acid is released after 150 minutes in the model system; and
e) from 75–100% of the total 5-aminosalicylic acid is released after 240 minutes in the model system.

2. A composition according to claim 1 having the following in vivo 5-aminosalicylic acid release parameters:
provided the gastric emptying is within the normal range, 50% of the granules have left the stomach within 60 minutes after intake of the composition.

3. A composition according to claim 1 having the following in vivo 5-aminosalicylic acid release parameters:
provided the small bowel transit time is within the normal range, 50% of the granules is present in the small bowel 3–6 hours after intake of the composition.

4. A composition according to claim 1 having the following in vivo 5-aminosalicylic acid release parameters:
provided the large bowel transit time is within the normal range, 50% of the granules is present in the large bowel 12–50 hours after intake of the composition.

5. A composition according to claim 1, wherein the percent by weight of 5-aminosalicylic acid of the total weight of said granule ranges from 30–90%.

6. A composition according to claim 1, wherein the 5-aminosalicylic acid is in a unit dosage form and comprises 5-aminosalicylic acid in amounts sufficient for the administration of from 250 mg to 12 g.

7. A composition according to claim 1, wherein the 5-aminosalicylic acid is supplied as unit dosage forms in sealed packages to be opened immediately prior to use.

8. A composition according to claim 1, wherein the inflammatory bowel disease is Crohn's disease, colitis ulcerosa, an unclassified form of said diseases, or a diagnosed subtype of said disease.

9. A method for the treatment of inflammatory bowel diseases, comprising orally administering an effective amount of a composition consisting essentially of:
individually coated granules, each granule comprising:
a core consisting essentially of 5-aminosalicylic acid or a pharamceutically acceptable salt or ester thereof and a physiologically acceptable spheronization aid, and
a coating confining said core, said coating comprising a rate-limiting barrier material; and
the majority of the granules being essentially spherical as defined by an aspect ratio from 1.00–1.25; and
the majority of the granules of the composition having sieve values in the range of ≧0.5 mm and <1.4 mm; and
the composition having the following in vitro dissolution rates when measured in a model system using simulated intestinal fluid in USP Paddle System 2 operated at 37° C. with a stirring speed of 100 rpm:
a) from 2–20% of the total 5-aminosalicylic acid is released after 15 minutes in the model system;
b) from 20–50% of the total 5-aminosalicylic acid is released after 60 minutes in the model system;
c) from 30–70% of the total 5-aminosalicylic acid is released after 90 minutes in the model system;
d) from 50–90% of the total 5-aminosalicylic acid is released after 150 minutes in the model system; and
e) from 75–100% of the total 5-aminosalicylic acid is released after 240 minutes in the model system.

10. A method according to claim 9, wherein the inflammatory bowel disease is Crohn's disease, colitis ulcerosa, an unclassified form of said diseases, or a diagnosed subtype of said disease.

11. A composition according to claim 1, wherein the spheronization aid is a cellulose derivative and the rate-limiting barrier material is a semi-permeable polymer.

12. A composition according to claim 1, wherein the spheronization aid is microcrystalline cellulose and the rate-limiting barrier material is ethylcellulose.

13. A composition according to claim 1, wherein more than 80% of the granules are essentially spherical as defined by an aspect ratio from 1.00–1.20.

14. A composition according to claim 1, wherein more than 90% of the granules are essentially spherical as defined by an aspect ratio from 1.00–1.15.

15. A composition according to claim 1, wherein more than 70% of the granules of the composition have sieve values in the range of ≧0.5 mm and <1.4 mm.

16. A composition according to claim 1, wherein more than 90% of the granules of the composition have sieve values in the range of ≧0.5 mm and <1.4 mm.

17. A composition according to claim 1, wherein the majority of the granules of the composition have sieve values in the range of 0.7 mm–1.1 mm.

18. A composition according to claim 1, wherein from 5–15% of the total 5-aminosalicylic acid is released after 15 minutes in the model system.

19. A composition according to claim 1, wherein from 25–45% of the total 5-aminosalicylic acid is released after 60 minutes in the model system.

20. A composition according to claim 1, wherein from 40–60% of the total 5-aminosalicylic acid is released after 90 minutes in the model system.

21. A composition according to claim 1, wherein from 55–80% of the total 5-aminosalicylic acid is released after 150 minutes in the model system.

22. A composition according to claim 1 having the following in vitro 5-aminosalicylic acid release parameters:
provided the gastric emptying is within the normal range, 50% of the granules have left the stomach within 30 minutes after intake of the composition.

23. A composition according to claim 1, wherein the percent by weight of 5-aminosalicylic acid of the total weight of said granule ranges from 40–80%.

24. A composition according to claim 1, wherein the percent by weight of 5-aminosalicylic acid of the total weight of said granule ranges from 50–60%.

25. A composition according to claim 1, wherein the 5-ASA is in a unit dosage form and comprises 5-aminosalicylic acid in amounts sufficient for the administration of from 500 mg to 6 g.

26. A composition according to claim 1, wherein the 5-ASA is in a unit dosage form and comprises 5-aminosalicylic acid in amounts sufficient for the administration of from 500 mg to 4 g.

27. A composition according to claim 9, wherein the spheronization aid is a cellulose derivative and the rate-limiting barrier material is a semi-permeable polymer.

28. A composition according to claim 9, wherein the spheronization aid is microcrystalline cellulose and the rate-limiting barrier material is ethylcellulose.

29. A method according to claim 9, wherein more than 80% of the granules are essentially spherical as defined by an aspect ratio from 1.00–1.20.

30. A method according to claim 9, wherein more than 90% of the granules are essentially spherical as defined by an aspect ratio from 1.00–1.15.

31. A method according to claim 9, wherein more than 70% of the granules of the composition have sieve values in the range of ≧0.5 mm and <1.4 mm.

32. A method according to claim 9, wherein more than 90% of the granules of the composition have sieve values in the range of ≧0.5 mm and <1.4 mm.

33. A composition according to claim 9, wherein the majority of the granules of the composition have sieve values in the range of 0.7 mm–1.1 mm.

34. A method according to claim 9, wherein from 5–15% of the total 5-aminosalicylic acid is released after 15 minutes in the model system.

35. A method according to claim 9, wherein from 25–45% of the total 5-ASA is released after 60 minutes in the model system.

36. A method according to claim 9, wherein from 40–60% of the total 5-aminosalicylic acid is released after 90 minutes in the model system.

37. A method according to claim 9, wherein from 55–90% of the total 5-aminosalicylic acid is released after 150 minutes in the model system.

* * * * *